United States Patent [19]

Shan et al.

[11] Patent Number: 5,958,697
[45] Date of Patent: Sep. 28, 1999

[54] ISOLATED NUCLEIC ACIDS ENCODING CYP7 PROMOTER-BINDING FACTORS

[75] Inventors: Bei Shan; Masahiro Nitta, both of South San Francisco, Calif.

[73] Assignees: Tularik Inc., South San Francisco, Calif.; Sumitomo Pharmaceuticals Co., Ltd., Japan

[21] Appl. No.: 09/132,619

[22] Filed: Aug. 11, 1998

Related U.S. Application Data

[60] Provisional application No. 60/067,708, Dec. 8, 1997.
[51] Int. Cl.$^6$ ................... C12Q 1/68; C12N 1/00; C12N 5/10; C12N 15/12; C12N 15/63; C12P 21/02
[52] U.S. Cl. ................ 435/6; 435/69.1; 435/243; 435/320.1; 435/325; 435/410; 536/23.5
[58] Field of Search ................. 536/23.1, 23.5; 530/324, 325, 326, 327, 328, 350; 435/320.1, 325, 420, 243, 69.1, 6

[56] References Cited

PUBLICATIONS

Kudo et al. Molecular cloning of chicken FTZ–F1–related orphan receptors. Gene. Sep. 15, 1997, vol. 197, No. ½, pp. 261–268.

Ellinger–Zeigelbauer et al, Molecular and Cellular Biology, vol. 14, No. 4: pp. 2786–2797, Apr. 1994.

*Primary Examiner*—Terry McKelvey
*Attorney, Agent, or Firm*—Richard Aron Osman

[57] ABSTRACT

The invention provides methods and compositions relating to CPF proteins which regulate transcriptional activation, and related nucleic acids. The polypeptides may be produced recombinantly from transformed host cells from the disclosed CPF encoding nucleic acids or purified from human cells. The invention provides isolated CPF hybridization probes and primers capable of specifically hybridizing with the disclosed CPF genes, CPF-specific binding agents such as specific antibodies, and methods of making and using the subject compositions in diagnosis, therapy and in the biopharmaceutical industry.

5 Claims, No Drawings

5,958,697

ISOLATED NUCLEIC ACIDS ENCODING CYP7 PROMOTER-BINDING FACTORS

This application claims the benefit of U.S. Provisional Application No. 60/067,708, filed Dec. 8, 1997, which is incorporated herein by reference.

FIELD OF THE INVENTION

The field of this invention is transcription factors which bind CYP7 promoters.

BACKGROUND

In mammalian cells, cholesterol is an essential component for membranogenesis and for the synthesis of sterols and nonsterols that are critical for normal cellular functions. Excess cholesterol, however, not only is lethal to cells but also creates a major problem in atherolsclerosis for its deposit in arteries. To maintain cholesterol homeostasis, cells, in particular liver cells, adopt three major ways to regulate cholesterol levels: 1) uptake of dietary cholesterol via LDL receptor; 2) endogenous cholesterol biosynthesis and 3) metabolic conversion of cholesterol to bile acids. The key molecule that coordinates these processes is cholesterol itself, serving as a feedback signal. When the intracellular cholesterol level increases either through cholesterol uptake or biosynthesis, the transcription of genes including LDL receptor and the key cholesterol biosynthesis enzymes such as HMG-CoA synthase and HMG-CoA reductase is repressed. These feedback processes are mediated by a novel family of transcription factors called sterol regulatory element binding proteins (SREBPs). SREBPs contain an N-terminal transcription factor domain, two hydrophobic transmembrane domains and a C-terminal regulatory domain. When the intracellular cholesterol level is low, a two-step proteolytic cascade occurs which releases the N-terminal transcription factor domain of SREBPs from the endoplasmic reticulum, moving to the nucleus where activation of the SRE-containing genes occurs.

While the SREBP pathway is responsible for regulation of genes involved in cholesterol uptake and cholesterol biosynthesis such as LDL receptor and HMG-CoA synthase, the molecular basis of cholesterol catabolism is largely unknown. The major catabolic pathway for cholesterol removal is the production of bile acids that occurs exclusively in the liver. Cholesterol 7α-hydroxylase is the first and rate-limiting enzyme in the pathway. The cholesterol 7α-hydroxylase gene, also known as CYP7, belongs to the cytochrome P-450 family that contains many microsomal enzymes involved in liver metabolism. It has been shown that the expression of the CYP7 gene is tightly regulated: it is expressed exclusively in liver; its expression can be induced by dietary cholesterol and suppressed by bile acids. It has been shown that cholesterol catabolism plays a central role in cholesterol homeostasis. Treatment of laboratory animals with cholestid or cholestyramine, two bile acid-binding resins, decreases serum cholesterol levels. Moreover, overexpression of the CYP7 gene in hamsters reduces total and LDL cholesterol levels. Thus, cholesterol 7α-hydroxylase is a potential therapeutic target for cholesterol lowering drugs and understanding the mechanisms by which expression of the CYP7 gene is regulated is of particular importance.

To study the molecular mechanisms of hepatic-specific expression of the human CYP7 gene, we used HepG2 cells as a model system since this cell line is one of the most studied hepatic cell lines and has been shown to be an appropriate cell line through studies of a number of hepatic-specific genes including the CYP7 gene. We started with DNase I hypersensitivity mapping of the human CYP7 promoter and identified a hepatic-specific element in the promoter. Consequently, we cloned the gene encoding the promoter-binding protein and identified it as a human ortholog of the nuclear orphan receptor Ftz-F1 family.

RELEVANT ART

Galarneau and Belanger (1997) unpublished, accession U93553, describe a human α1-Fetoprotein Transcription Factor (hFTF, SEQ ID NOS:7 and 8); Tugwood,J. D., Issemann,I. and Green,S. (1991) unpublished, accession M81385, describe a mouse liver receptor homologous protein (LRH-1) mRNA and conceptual translate (mLRH, SEQ ID NOS:9 and 10); and L. Galarneau et al. (1996) Mol. Cell Biol. 16, 3853–3865 disclose a partial rat gene; all having sequence similarity to the disclosed CPF polypeptides.

SUMMARY OF THE INVENTION

The invention provides methods and compositions relating to isolated CPF polypeptides, related nucleic acids, polypeptide domains thereof having CPF-specific structure and activity and modulators of CPF function, particularly CYP7 promoter binding. CPF polypeptides can regulate CYP7 promoter-linked gene activation and hence provide important regulators of cell function. The polypeptides may be produced recombinantly from transformed host cells from the subject CPF polypeptide encoding nucleic acids or purified from mammalian cells. The invention provides isolated CPF hybridization probes and primers capable of specifically hybridizing with the disclosed CPF gene, CPF-specific binding agents such as specific antibodies, and methods of making and using the subject compositions in diagnosis (e.g. genetic hybridization screens for CPF transcripts), therapy (e.g. CPF activators to activate CYP7 promoter-dependent transcription) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequence of natural cDNAs encoding human CPF polypeptides are shown as SEQ ID NOS: 1, 3 and 5, and the full conceptual translates are shown as SEQ ID NOS:2, 4 and 6, respectively. The CPF polypeptides of the invention include one or more functional domains of SEQ ID NO:2, 4 or 6, which domains comprise at least 8, preferably at least 16, more preferably at least 32, most preferably at least 64 contiguous residues of SEQ ID NO:2, 4 or 6 and have human CPF-specific amino acid sequence and activity. CPF domain specific activities include CYP7 promoter-binding or transactivation activity and CPF specific immunogenicity and/or antigenicity. CPF specific polypeptide sequences distinguish hFTF and mLRH (SEQ ID NOS:8 and 10), and are readily identified by sequence comparison; see, e.g. Tables 5, 6, and 7 herein. Exemplary sequences include 10 residue domains of SEQ ID NO:2 comprising at least one of residues 1–10, 11–15, 16–21, 204–207 and 299–307, 10 residue domains of SEQ ID NO:4 comprising residue 154, and 10 residue domains of SEQ ID NO:6 comprising at least one of residues 3–10, 13–22 and 30–38.

CPF-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an CPF polypeptide with a binding target is evaluated. The binding target may be a natural intracellular binding target such as a CYP7 promoter binding site, a CPF regulating protein or other regulator that directly modulates CPF activity or its localization; or non-natural binding target such as a specific immune protein such as an antibody, a synthetic nucleic acid binding site (see consensus sequences, below), or a CPF specific agent such as those identified in screening assays such as described below. CPF-binding specificity may be assayed by binding equilibrium constants (usually at least about $10^7$ M$^{-1}$, preferably at least about $10^8$ M$^{-1}$, more preferably at least about $10^9$ M$^{-1}$), by CYP7 or syntheic binding site reporter expression, by the ability of the subject polypeptides to function as negative mutants in CPF-expressing cells, to elicit CPF specific antibody in a heterologous host (e.g a rodent or rabbit), etc. For example, in this fashion, domains defined by SEQ ID NO:2, residues 33–123 are shown to provide a functional DNA binding domain, and those defined by SEQ ID NO:2, residues 242–333 and 383–405 are shown to provide a functional ligand binding domain.

In a particular embodiment, deletion mutagenesis is used to define functional CPF domains which bind CYP7 promoter elements (see Examples, below). See, e.g. Table 1.

TABLE 1

Exemplary CPF deletion mutants defining CPF functional domains.

| Mutant | Seguence | DNA binding |
|---|---|---|
| ΔN1 | SEQ ID NO:2, residues 4–495 | + |
| ΔN2 | SEQ ID NO:2, residues 12–494 | + |
| ΔN3 | SEQ ID NO:2, residues 24–495 | + |
| ΔN4 | SEQ ID NO:2, residues 33–495 | + |
| ΔN5 | SEQ ID NO:2, residues 33–123 | + |
| ΔC1 | SEQ ID NO:2, residues 1–408 | + |
| ΔC2 | SEQ ID NO:2, residues 1–335 | + |
| ΔC3 | SEQ ID NO:2, residues 1–267 | + |
| ΔC4 | SEQ ID NO:2, residues 1–189 | + |
| ΔC5 | SEQ ID NO:2, residues 1–124 | + |

In a particular embodiment, the subject domains provide CPF-specific antigens and/or immunogens, especially when coupled to carrier proteins. For example, peptides corresponding to CPF- and human CPF-specific domains are covalently coupled to keyhole limpet antigen (KLH) and the conjugate is emulsified in Freunds complete adjuvant. Laboratory rabbits are immunized according to conventional protocol and bled. The presence of CPF-specific antibodies is assayed by solid phase immunosorbant assays using immobilized CPF polypeptides of SEQ ID NO:2, 4 or 6, see, e.g. Table 2.

TABLE 2

Immunogenic CPF polypeptides eliciting CPF-specific rabbit polyclonal antibody: CPF polypeptide-KLH conjugates immunized per protocol described above.

| CPF Polypeptide Sequence | Immunogenicity |
|---|---|
| SEQ ID NO:2, residues 1–10 | +++ |
| SEQ ID NO:2, residues 4–15 | +++ |
| SEQ ID.NO:2, residues 8–20 | +++ |
| SEQ ID NO:2, residues 12–25 | +++ |
| SEQ ID NO:2, residues 15–30 | +++ |

TABLE 2-continued

Immunogenic CPF polypeptides eliciting CPF-specific rabbit polyclonal antibody: CPF polypeptide-KLH conjugates immunized per protocol described above.

| CPF Polypeptide Sequence | Immunogenicity |
|---|---|
| SEQ ID NO:2, residues 19–32 | +++ |
| SEQ ID NO:2, residues 20–29 | +++ |
| SEQ ID NO:2, residues 200–211 | +++ |
| SEQ ID NO:4, residues 150–159 | +++ |

The claimed CPF polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The CPF polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides binding agents specific to CPF polypeptides, preferably the claimed CPF polypeptides, including agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins, e.g.CYP7 promoter-dependent transcriptional activation. Novel CPF-specific binding agents include CPF-specific receptors/CPF-specific binding proteins, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one, two- and three-hybrid screens, non-natural intracellular binding agents identified in screens of chemical libraries such as described below, etc. Agents of particular interest modulate CPF function, e.g. CPF-dependent transcriptional activation.

Accordingly, the invention provides methods for modulating signal transduction involving a CPF or a CYP7 promoter in a cell comprising the step of modulating CPF activity. The cell may reside in culture or in situ, i.e. within the natural host. For diagnostic uses, CPF binding agents are frequently labeled, such as with fluorescent, radioactive, chemiluminescent, or other easily detectable molecules, either conjugated directly to the binding agent or conjugated to a probe specific for the binding agent. Exemplary inhibitors include nucleic acids encoding dominant/negative mutant forms of CPF, as described above, etc.

The amino acid sequences of the disclosed CPF polypeptides are used to back-translate CPF polypeptide-encoding nucleic acids optimized for selected expression systems (Holler et al. (1993) Gene 136, 323–328; Martin et al. (1995)

Gene 154, 150–166) or used to generate degenerate oligonucleotide primers and probes for use in the isolation of natural CPF-encoding nucleic acid sequences ("GCG" software, Genetics Computer Group, Inc, Madison Wis.). CPF-encoding nucleic acids used in CPF-expression vectors and incorporated into recombinant host cells, e.g. for expression and screening, transgenic animals, e.g. for functional studies such as the efficacy of candidate drugs for disease associated with CPF-modulated cell function, etc.

The invention also provides nucleic acid hybridization probes and replication/amplification primers having a CPF cDNA specific sequence comprising at least 12, preferably at least 24, more preferably at least 36 and most preferably at least contiguous 96 bases of a strand of SEQ ID NO: 1, 3 or 5 sufficient to specifically hybridize with a second nucleic acid comprising the complementary strand of SEQ ID NO: 1, 3 or 5 and distinguish hFTF and mLRH cDNAs (SEQ ID NOS:7 and 9). Such CPF specific sequences are readily discernable by sequence comparison; see, e.g. Table 8, herein. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C.

TABLE 3

Exemplary CPF nucleic acids which hybridize with a strand of SEQ ID NO: 1, 3 and/or 5 under Conditions I and/or II.

| CPF Nucleic Acids | Hybridization |
| --- | --- |
| SEQ ID NO:1, nucleotides 1–26 | + |
| SEQ ID NO:1, nucleotides 52–62 | + |
| SEQ ID NO:1, nucleotides 815–825 | + |
| SEQ ID NO:1, nucleotides 1120–1135 | + |
| SEQ ID NO:1, nucleotides 1630–1650 | + |
| SEQ ID NO:1, nucleotides 1790–1810 | + |
| SEQ ID NO:1, nucleotides 1855–1875 | + |
| SEQ ID NO:1, nucleotides 1910–1925 | + |
| SEQ ID NO:1, nucleotides 2090–2110 | + |
| SEQ ID NO:1, nucleotides 2166–2186 | + |
| SEQ ID NO:1, nucleotides 2266–2286 | + |
| SEQ ID NO:1, nucleotides 2366–2386 | + |
| SEQ ID NO:1, nucleotides 2466–2486 | + |
| SEQ ID NO:1, nucleotides 2566–2586 | + |
| SEQ ID NO:1, nucleotides 2666–2686 | + |
| SEQ ID NO:1, nucleotides 2766–2786 | + |
| SEQ ID NO:1, nucleotides 2866–2886 | + |
| SEQ ID NO:1, nucleotides 2966–2986 | + |
| SEQ ID NO:1, nucleotides 3066–3086 | + |

The subject nucleic acids are of synthetic/non-natural sequences and/or are isolated, i.e. unaccompanied by at least some of the material with which they are associated in their natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than those which they are joined to on a natural chromosome. Recombinant nucleic acids comprising the nucleotide sequence of SEQ ID NO: 1, 3 or 5, or requisite fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of CPF genes and gene transcripts and in detecting or amplifying nucleic acids encoding additional CPF homologs and structural analogs. In diagnosis, CPF hybridization probes find use in identifying wild-type and mutant CPF alleles in clinical and laboratory samples. Mutant alleles are used to generate allele-specific oligonucleotide (ASO) probes for high-throughput clinical diagnoses. In therapy, therapeutic CPF nucleic acids are used to modulate cellular expression or intracellular concentration or availability of active CPF.

The invention provides efficient methods of identifying agents, compounds or lead compounds for agents active at the level of a CPF modulatable cellular function. Generally, these screening methods involve assaying for compounds which modulate CPF interaction with a natural CPF binding target. A wide variety of assays for binding agents are provided including labeled in vitro protein-protein binding assays, immunoassays, DNA-binding assay, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including a CPF polypeptide, which may be part of a fusion product with another peptide or polypeptide, e.g. a tag for detection or anchoring, etc. The assay mixtures comprise a natural intracellular CPF binding target. While native full-length binding targets may be used, it is frequently preferred to use portions (e.g. oligonucleotides) thereof so long as the portion provides binding affinity and avidity to the subject CPF polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the CPF polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the CPF polypeptide and one or more binding targets is detected by any convenient way. A difference in the binding affinity of the CPF polypeptide to the target in the absence of the agent as compared with the binding affinity in the presence of the agent indicates that the agent modulates the binding of the CPF polypeptide to the CPF binding target. Analogously, in the cell-based assay also described below, a difference in CPF-dependent transcriptional activation in the presence and absence of an agent indicates the agent modulates CPF function. A difference, as used herein, is statistically significant and preferably represents at least a 50%, more preferably at least a 90% difference.

The following experimental section and examples are offered by way of illustration and not by way of limitation.

EXAMPLES

1. Isolation and Characterization of CPF and CYP7 promoter elements

Cells and Plasmids HepG2, a human hepatoma cell line, 293, a transformed embryonic kidney cell line, and Caco2, a colon adenocarcinoma cell line are purchased from ATCC. SV589 is a transformed human fibrablast line. Cells were cultured in Dulbecco's modified Eagle's medium-Ham's F12 (1:1) supplemented with 10% fetal calf serum at 37° C., 5%CO in a humidified incubator. pGL3:CYP7 contains a DNA fragment of −716/+14 region of the human CYP7α gene, which was cloned into the pGL3-luciferase reporter plasmid (Promega). pGL3:SFM or pGL3:BAM contains mutations at the positions of -130 and -129 (GG to TT) or of -62 and -61 (AA to TC) respectively. The two base pair substitutions were introduced into pGL3:CYP7 by using ExSite mutagenesis kit (Stratagene). pGL3 :3xwt and pGL3:3xmut were constructed by cloning three tendon repeats of either wild type of - 135 to -118 of the promoter or the repeats with two base pair substitutions of G to T at the positions of-1 30 and -129 into a modified pGL3 with an TATA sequence from the HSV TK gene. pfCPF contains a flag tagged sequence at the N terminus of the gene which was cloned into pCDNA3 (Invitrogene). pfCPF-AF2 has an 15 amino acid deletion of the AF-2 domain at the C terminus of the gene. pfCPF-VP contains a transactivation domain (aa412–490) of HSV VP16 which replaces the AF-2 domain of pfCPF.

Dnase I hypersensitivity mapping Cells ($3 \times 10^6$) were harvested and lysed in 1.5 ml of lysis buffer containing 50 mM Tris-HCl pH 7.9, 100 MM KCl, 5 mM $MgCl_2$, 0.05% saponin, 200 mM 2-mercaptoethanol, 50% glycerol. Nuclei were collected by centrifugation and resuspended in the buffer containing 100 mM NaCl, 50 mM Tris-HCl pH 7.9, 3 mM $MgCl_2$, 1 mM DTT, 1X complete protease inhibitor cocktail (3oeringer Mannheim), and sequentially diluted DNase I (5, 1.7, 0.6 units/ml). Nuclei suspensions were incubated at 37° C. for 20 min. The reactions were stopped by adding EDTA to a final concentration of 100 mM. After RNase A and Protease K treatment, genomic DNA was prepared and subjected to southern hybridization.

Electrophoretic mobility shift assay Nuclear extracts were prepared from cultured cells using KCl instead of NaCl. In vitro transcription and translation were performed with a TNT system (Promega). 1 $\mu$g of protein of nuclear extracts or 0.1~1 $\mu$l of in vitro translated product was mixed with 40,000 cpm of $^{32}P$ labeled oligonucleotide in the reaction buffer containing 10 mM Hepes (pH7.6), 1 $\mu$g of poly (dI-dC), 100 mM KCl, 7 % glycerol, 1 mM EDTA, 1 mM DTT, 5 mM $MgCl_2$, and 40 pmoles unrelated single strand oligo DNA, and incubated for 20 min at room temperature. Reaction mixtures were separated on 4 % polyacrylamide-0.5×TBE gel. Gels were dried and exposed to X-ray films. In competition experiments, 30 or 60 fold molar excess of competitor DNA was added. In antibody supershift experiments, an anti-CPF antiserum or pre-immune serum was added to the reaction mixtures prior to the addition of probe DNA.

Transfection and reporter gene analysis One day before transfection, cells were plated on 6-well dishes ($4 \times 10^5$/well). In general, 2 ug of luciferase reporter plasmid along with 0.1 ug of RSV LTR driven b-galactosidase expression vector was transfected by the calcium phosphate method into cultuered cells for 48 hours. Cell extracts were prepared and assayed for the luciferase activity using Luciferase assay system (Promega). Luciferase activity was normalized by the b-galactosidase activity.

Molecular cloning of CPF. A human EST clone (GenBank accession number N59515) which contains the Ftz-F1 box sequence was used to screen a human liver cDNA library purchased from Clontech. cDNAs in positive clones were recovered by conversion of phage DNA into pTriplEx plasmids and sequenced. Among several positive clones which might be alternative spliced forms from the same gene, one clone (pTriplEx-113) was selected for further analysis.

Tissue-specific expression of CPF. Northern blots of polyA+RNA from human tissues were purchased from Clontech. Hybridization reaction was carried out with the Northern MAX hybridization buffer (Ambion).

Immunoprecipitation. Peptide derived from CPF cDNA sequence (DRMRGGRNFKGPMYKRDR) (SEQ ID NO:6, residues 159–176) was used to raise an anti-CPF polyclonal antibody. HepG2 or 293 cells ($1 \times 10^7$) were cultured in the media containing 100 $\mu$Ci/ml of $^{35}S$-methionine for 30 min. Cells were harvested and lysed by 3 times of freeze-thaw in the buffer containing 50 mM Tris-HCl pH7.5, 125 mM NaCl, 5 mM EDTA, 0.1% NP-40. Cell lysates were then used for immunoprecipitation with the anti-CPF antibody. Precipitated samples were separated by 10% SDS-PAGE and exposed to X-ray films.

Dnase I hypersensitive site mapping of the human CYP7 gene. To study the mechanisms of hepatic-specific expression of the human CYP7 gene, we first attempted to identify the putative elements responsible for the hepatic-specific expression by DNase I hypersensitivity mapping of the gene. DNase I hypersensitivity is known to be associated with the activity of transcription. Nuclei prepared from HepG2, 293 and Caco2 cells were treated with the increasing amount of DNase I. DNA was then extracted, digested with the proper restriction enzymes, and probed by Southern blotting with a labeled fragment containing nucleotide from -944 to -468. In addition to a predicted 5 kb Pst I fragment, a second 2.8 kb band was observed. The increased intensity of the 2.8 kb band, accompanied by the decreased intensity of the parental 5 kb band in parallel with the increased amount of DNase I treatment, indicated the existence of a DNase I hypersensitive site. Importantly, the 2.8 kb band was only shown in HepG2 cells but not in other cells examined. The size of the fragment indicates that the hepatic-specific DNase I hypersensitive site is localized between -100 bp to -300 bp relative to the transcriptional initiation site of the human CYP7 gene. The location of the site was further confirmed by using different restriction enzymes with probes from different regions.

Identification of a hepatic-specific CYP7 promoter element. To further identify the hepatic-specific element of the CYP7 gene, seven overlapped oligonucleotides (CL5, bp -368–291; CL6, bp -311–232; CL7, bp -256–177; CLI, bp -201–122; CL2, bp -140–61; CL3, bp -121–42; CL4, bp -60-+20) were synthesized and used in gel mobility shift experiments. There were hepatocytic-specific DNA-protein complexes formed when labeled oligonucleotide CL1 and oligonucleotide CL2 were used. The oligonucleotides CL1 and CL2 apparently recognized the same complex since unlabeled oligonucleotide CL1 competed with oligonucleotide CL2. This DNA-protein complex is sequence specific since they can be competed by excess of unlabeled oligonucleotides CL1 and CL2, but not by oligonucleotides next to this region, CL3–7. This promoter complex was observed only with HepG2 nuclear extracts but not with 293, Caco2 or SV589 nuclear extracts, consistent with the hepatic-specific DNase I hypersensitive site identifed above. The sequence overlapped with these two oligonucleotides is apparently responsible for the hepatic-specific DNA-protein complex.

Sequence analysis revealed that this region contains several six bp repeated elements, known to be the binding sites for nuclear hormone receptors. To determine the exact sequences responsible for the hepatic-specific binding, several oligonucleotides that contain mutations in each of the repeats or adjacent sequences were synthesized. As shown in Table 4, while oligonucleotides containing mutations in repeats A and B competed complex formation, oligonucleotides containing mutations in repeat C failed to compete, indicating that repeat C is essential for the binding. To further determine the nucleotides required for complex formation, a number of oligonucleotides containing detailed mutations in repeat C and adjacent sequences were synthesized and used in gel shift experiments. Our results indicated that a consensus element containing nine nucleotides is required for the complex formation. This element is known to be a binding site for a family of nuclear hormone receptor called Ftz-F1.

TABLE 4

| Oligonucleotide | DNA Binding |
|---|---|
| TCTGATACCTGTGGACTTAGTTCAAGGCCAGTTA (SEQ ID NO:11) | + |
| TCTG<u>GAGGA</u>TGTGGACTTAGTTCAAGGCCAGTTA (SEQ ID NO:12) | + |
| TCTGATACCTGT<u>TATAT</u>TAGTTCAAGGCCAGTTA (SEQ ID NO:13) | + |
| TCTGGAGGATGTGGACTT<u>CTAT</u>CAAGGCCAGTTA (SEQ ID NO:14) | + |
| TCTGATACCTGT<u>TATAT</u>T<u>CTAT</u>CAAGGCCAGTTA (SEQ ID NO:15) | + |
| TCTGGAGGATGTGGACTTAGTTCA<u>CACAGAG</u>TTA (SEQ ID NO:16) | + |
| TCTGATACCTGTGGACTTAGT<u>AG</u>AAGGCCAGTTA (SEQ ID NO:17) | – |
| TCTGATACCTGTGGACTTAGTTC<u>TT</u>GGCCAGTTA (SEQ ID NO:18) | – |
| TCTGATACCTGTGGACTTAGTTCAA<u>T</u>GCCAGTTA (SEQ ID NO:19) | – |
| TCTGATACCTGTGGACTTAGTTCAAG<u>T</u>CCAGTTA (SEQ ID NO:20) | – |
| TCTGATACCTGTGGACTTAGTTCAAGG<u>AG</u>AGTTA (SEQ ID NO:21) | – |
| TCTGATACCTGTGGACTTAGTTCAAGGCC<u>TA</u>TTA (SEQ ID NO:22) | – |
| TCTGATACCTGTGGACTTAGTTCAAGGCCA<u>A</u>TTA (SEQ ID NO:23) | + |
| TCTGATACCTGTGGACTTAGTTCAAGGCCAG<u>G</u>TA (SEQ ID NO:24) | + |
| TCAAGGCCA | CYP7P-Binding Site |
| YCAAGGYCR | FTZ-F1 consensus |
| AAAGGTCA | NGPI-B consensus |
| TCTGATACCTGTGGACTTAGT<u>C</u>AAAGGCCAGTTA (SEQ ID NO:25) | – |
| TCTGATACCTGTGGACTTAGTA<u>CC</u>AGGCCAGTTA (SEQ ID NO:26) | – |
| TCTGATACCTGTGGACTTAGTA<u>GG</u>AGGCCAGTTA (SEQ ID NO:27) | – |
| TCTGATACCTGTGGACTTAGTA<u>A</u>GAGGCCAGTTA (SEQ ID NO:28) | – |
| TCTGATACCTGTGGACTTAGTTT<u>C</u>AGGCCAGTTA (SEQ ID NO:29) | – |
| TCTGATACCTGTGGACTTAGT<u>CTC</u>AGGCCAGTTA (SEQ ID NO:30) | – |

Ftz-F1 binding site is essential for the hepatic-specific expression of the human CYP7 gene. To determine the role of the Ftz-F1 site in human CYP7 gene expression, the site was mutated by 2 nucleotide substitutions. As a control, mutations at an unrelated region were also created. The promoter sequence of +14 to −716 containing either the wild type or mutated Ftz-F 1 site, or control was cloned into a luciferase reporter plasmid pGL3. The plasmid DNA was then transfected into HepG2, 293 and Caco2 cells and promoter activity was measured by luciferase activity. Mutations in the Ftz-F1 site completely abolished promoter activity in HepG2 cells while showing little or no effects on 293 and Caco2 cells. As a control, mutations in the unrelated region showed no effect on promoter activity in all cells examined.

Cloning of the hepatic-specific CYP7 promoter-binding protein. Nuclear hormone receptors are DNA-specific, often ligand-dependent, transcription factors. Ftz-F1, a drosophila DNA-binding protein, is the prototype of a subgroup of the nuclear hormone receptor family. Like most of the nuclear hormone receptors, Ftz-F1 contains a zinc finger DNA-binding domain and a putative ligand-binding domain. The DNA-binding domain of the Ftz-F1 family members contains a unique 26 amino acid extension (called Ftz-F1 box) at C terminus of the two zinc finger modules. The sequence of Ftz-F1 box is conserved from drosophila to rodent, and is largely responsible for the sequence-specific binding to DNA. The identification of the Ftz-F1 binding site in the human CYP7 promoter suggests that a human Ftz-F1-like protein binds to the Ftz-F1 element in the human CYP7 gene. To clone the human version of Ftz-F1, a DNA sequence of the Ftz-F1 box was used to search an EST database and a human EST clone was found. This EST sequence was then used as the probe to screen a human liver cDNA library. Several clones were isolated and one of them, clone #113, was used for further analysis.

Characterization of CPF. Clone #113 encodes a full length polypeptyde of 495 amino acids, with an in-frame stop codon 30 nucleotides upstream of the first ATG. We named the protein as CPF for CYP7 Promoter-binding Eactor. Sequence analysis reveals that CPF is a new member of the Ftz-F1 family. The closest homologs of CPF are the mouse version of the family, LRH-1 (SEQ ID NOS:7, 8)and a human variant, hFTF (SEQ ID NOS:9, 10). To confirm the cloned CPF is the factor responsible for the CYP7 promoter binding activity, in vitro translated CPF was used side-by-side with the HepG2 nuclear extracts in gel shift experiments. We found in vitro translated CPF recognized the same DNA sequence as the endogenous protein does and the gel shift patterns between these two appear to be identical. Antibodies raised against a peptide containing the Ftz-F1 box were used in gel shift experiments. We found the DNA-protein complex formed either with HepG2 nuclear extracts or with in vitro translated CPF was disrupted by the specific antibody but not by preimmune serum. Furthermore, the antibody recognized a hepatic-specific cellular protein that comigrates with the in vitro translated CPF. The endogenous gene product recognized by the Ftz-F1-specific antibody is apparently hepatic specific since there is no corresponding protein in 293 cells.

Transcriptional activity of CPF. To determine the transcriptional activity of CPF, flag tagged expression plasmid pfCPF was used to be transfected into 293 cells with luciferase reporter plasmids containing three copies of wild type Ftz-F1 binding site. We found pfCPF has a limited transcriptional activity. To determine whether the weak transcriptional activity is due to the weak transcription domain AF2 of the gene whose activity is probably also ligand dependent, pfCPF-VP was constructed by replacing the AF2 domain of CPF with a strong viral transactivation domain. When FCPF-VP was tranfected into 293 cells together with the reporter plasmid, a strong transcriptional activity was observed, suggesting that transcriptional activation of CPF requires help from either a ligand-dependent process or a cofactor.

Tissue specific expression of CPF. It has been reported that in rodents CYP7 gene is exclusively expressed in liver. To determine the tissue specific expression of the CPF gene, a pair of RNA tissue blots were probed either with labeled CPF cDNA or with CYP7 cDNA. We found the expression of the CPF gene apparently enriched in pancreas and liver, with a low level of expression in heart and lung, and little or no expression in other tissues. The human CYP7 is apparently expressed only in liver. Interestingly, a pancreas-specific transcript with a lower molecular weight was recognized by the human CYP7 probe.

2. High-Throughput In Vitro Fluorescence Polarization Assay

Reagents:
  Sensor: Rhodamine-labeled ILRKLLQE peptide (final conc.=1–5 nM)
  Receptor: Glutathione-S-transferase/CPF ligand binding domain (SEQ ID NO:2, residues 1–123) fusion protein (final conc.=100–200 nM)
  Buffer: 10 mM HEPES, 10 mM NaCl, 6 mM magnesium chloride, pH 7.6

Protocol:
  1. Add 90 microliters of Sensor/Receptor mixture to each well of a 96-well microtiter plate.
  2. Add 10 microliters of test compound per well.
  3. Shake 5 min and within 5 minutes determine amount of fluorescence polarization by using a Fluorolite FPM-2 Fluorescence Polarization Microtiter System (Dynatech Laboratories, Inc).

3. Protocol for Cell-Based Reporter Assay

CPF can trans-activate FTZ-F1 reporter constructs when overexpressed in 293 cells or HeLa cells. 293 cells are transfected using the calcium phosphate precipitation method with a plasmid encoding a 3 FTZ-F1 binding site-luciferase reporter construct and various amounts of expression vector encoding CPF. After 36–48 hours, cells are left untreated or treated with candidate ligand (10–50 ng/ml) for 6 hours prior to harvest. Cells are lysed and luciferase activity measured using the luciferase assay kit (Promega). The luciferase activity in each transfection is normalized by co-transfecting a pRSV-β gal control vector.

4. Sequence Alignments

Various alignments of the subject polynucleotide and polypeptide sequences are shown in Tables 5–8, revealing sequence-specific fragments. For example, Table 7 shows an alignment of 105, hFTF and mLRH polypeptide sequences revealing 105-, hFTF- and mLRH-specific peptides. An analogous alignment of their respective cDNA sequences (SEQ ID NOS:5, 7 and 9, respectively) reveals 105-, HFTF- and mLRH-specific cDNA fragments.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 5

```
113PRO    MSSNSDTGDL QESLKHG--- -LTP--IVSQ FKMVNYSYDE DLEELCPVCG  44 hFTFpro   MLPKVETEAL GLARSHGEQG QMPENMQVSQ FKMVNYSYDE DLEELCPVCG  50

113PRO    DKVSGYHYGL LTCESCKGFF KRTVQNNKRY TCIENQNCQI DKTQRKRCPY  94 hFTFpro   DKVSGYHYGL LTCESCKGFF KRTVQNNKRY TCIENQNCQI DKTQRKRCPY 100

113PRO    CRFQKCLSVG MKLEAVRADR MRGGRNKFGP MYKRDRALKQ QKKALIRANG 144 hFTFpro   CRFQKCLSVG MKLERVRADR MRGGRNKFGP MYKRDRALKQ QKKALLRANG 150

113PRO    LKLEAMSQVI QAMPSDLTIS SAIQNIHSAS KGLPLNHAAL PPTDYDRSPF 194 hFTFpro   LKLEAMSQVI QAMPSDLTIS SAIQNIHSAS KGLPLNHAAL PPTDYDRSPF 200

113PRO    VTSPISMTMP PHGSLQGYQT YGHFPSRAIK SEYPDPYTSS PESIMGYSYM 244 hFTFpro   VTSPISMTM- LHGSLQGYQT YGHFPSRAIK SEYPDPYTSS PESIMGYSTM 249

113PRO    DSYQTSSPAS IPHLILELLK CEPDEPQVQA KIMAYLQQEQ ANRSKHEKLS 294 hFTFpro   DSYQTSSPAS IPHLILELLK CEPDEPQVQA KIMAYLQQEQ ANRSKHEKLS 299

113PRO    TFGLMCKMAD QTLFSIVEWA RSSIFFRELK VDDQMKLLQN CWSELLILDH 344 hFTFpro   TFGLMCKMAD QTVFSIVEWA RSSIFFRELK VDDQMKLLQN CWSELLILDH 349

113PRO    IYRQVVHGKE GSIFLVTGQQ VDYSIIASQA GATLNNLMSH AQELVAKLRS 394 hFTFpro   IYRQVVHGKE GSIFLVTGQQ VDYSIIASQA GATLNNLMSH AQELVAKLRS 399

113PRO    LQFDQREFVC LKFLVLFSLD VKNLENFQLV EGVQEQVNAA LLDYTMCNYP 444 hFTFpro   LQFDQREFVC LKFLVLFSLD VKNLENFQLV EGVQEQVNAA LLDYTMCNYP 449

113PRO    QQTEKFGQLL LRLPEIRAIS MQAEEYLYYK HLNGDVPYNN LLIEMLHAKR 494 hFTFpro   QQTEKFGQLL LRLPEIRAIS MQAEEYLYYK HLNGDVPYNN LLIEMLHAKR 499

113PRO    A                                                      495 hFTFpro   A                                                      500
```

113PRO = SEQ ID NO:2
hFTFpro = SEQ ID NO:8

TABLE 6

```
113PRO    MSSNSDTGDL QESLKHG--- ---------- ---------- ----------  17

36pro     MSSNSDTGDL QESLKHG--- ---------- ---------- ----------  17 hFTFpro   MLPKVETEAL GLARSHG--- ---------- ---------- ----------  17 mLRHpro   MSASLDTGDF QEFLKHGLTA IASAPGSETR HSPKREEQLR EKRAGLPDRH  50

113PRO    ---------- ---------- ---------- --LTP--IVS QFKMVNYSYD  33

36pro     ---------- ---------- ---------- --LTP--IVS QFKMVNYSYD  33 hFTFpro   ---------- ---------- --------EQ GQMPENMQVS QFKMVNYSYD  39 mLRHpro   RRPIPARSRL VMLPKVETEA PGLVRSHGEQ GQMPENMQVS QFKMVNYSYD 100

113PRO    EDLEELCPVC GDKVSGYHYG LLTCESCKGF FKRTVQNNKR YTCIENQNCQ  83

36pro     EDLEELCPVC GDKVSGYHYG LLTCESCKGF FKRTVQNNKR YTCIENQNCQ  83 hFTFpro   EDLEELCPVC GDKVSGYHYG LLTCESCKGF FKRTVQNNKR YTCIENQNCQ  89 mLRHpro   EDLEELCPVC GDKVSGYHYG LLTCESCKGF FKRTVQNQKR YTCIENQNCQ 150

113PRO    IDKTQRKRCP YCRFQKCLSV GMKLEAVRAD RMRGGRNKFG PMYKRDRALK 133

36pro     IDKTQRKRCP YCRFQKCLSV GMKLEAVRAD RMRGGRNKFG PMYKRDRALK 133
```

TABLE 6-continued

```
hFTFpro  IDKTQRKRCP YCRFQKCLSV GMKLEAVRAD RMRGGRNKFG PMYKRDRALK 139
mLRHpro  IDKTQRKRCP YCRFKKCIDV GMKLEAVRAD RMRGGRNKFG PMYKRDRALK 200

113PRO   QQKKALIRAN GLKLEAMSQV IQAMPSDLTI SSAIQNIHSA SKGLPLNHAA 183
36pro    QQKKALIRAN GLKLEAMSQV D--------- ---------- ---------- 154
hFTFpro  QQKKALIRAN GLKLEAMSQV IQAMPSDLTI SSAIQNIHSA SKGLPLNHAA 189
mLRHpro  QQKKALIRAN GLKLEAMSQV IQAMPSDLT- -SAIQNIHSA SKGLPLSHVA 248

113PRO   LPPTDYDRSP FVTSPISMTM PPHGSLQGYQ TYGHFPSRAI KSEYPDPYTS 233
36pro    ---------- ---------- ---------- ---------- ---------- 154
hFTFpro  LPPTDYDRSP FVTSPISMTM -LHGSLQGYQ TYGHFPSRAI KSEYPDPYTS 238
mLRHpro  LPPTDYDRSP FVTSPISMTM PPHSSLHGYQ PYGHFPSRAI KSEYPDPYSS 298

113PRO   SPESIMGYSY MDSYQTSSPA SIPHLILELL KCEPDEPQVQ AKIMAYLQQE 283
36pro    ---------- ---------- ---------- ---------- ---------- 154
hFTFpro  SPESIMGYSY MDSYQTSSPA SIPHLILELL KCEPDEPQVQ AKIMAYLQQE 288
mLRHpro  SPESMMGYSY MDGYQTNSPA SIPHLILELL KCEPDEPQVQ AKIMAYLQQE 348

113PRO   QANRSKHEKL STFGLMCKMA DQTLFSIVEW ARSSIFFREL KVDDQMKLLQ 333
36pro    ---------- ---------- ---------- ---------- ---DQMKLLQ 161
hFTFpro  QANRSKHEKL STFGLMCKMA DQTVFSIVEW ARSSIFFREL KVDDQMKLLQ 338
mLRHpro  QSNRNRQEKL SAFGLLCKMA DQTLFSIVEW ARSSIFFREL KVDDQMKLLQ 398

113PRO   NCWSELLILD HIYRQVVHGK EGSIFLVTGQ QVDYSIIASQ AGATLNNLMS 383
36pro    NCWSELLILD HIYRQVVHGK EGSIFLVTGQ QVDYSIIASQ AGATLNNLMS 211
hFTFpro  NCWSELLILD HIYRQVVHGK EGSIFLVTGQ QVDYSIIASQ AGATLNNLMS 388
mLRHpro  NCWSELLILD HIYRQVAHGK EGTIFLVTGE HVDYSTIISH TEVAFNNLLS 448

113PRO   HAQELVAKLR SLQFDQREFV CLKFLVLFSL DVKNLENFQL VEGVQEQVNA 433
36pro    HAQELVAKLR SLQFDQREFV CLKFLVLFSL DVKNLENFQL VEGVQEQVNA 261
hFTFpro  HAQELVAKLR SLQFDQREFV CLKFLVLFSL DVKNLENFQL VEGVQEQVNA 438
mLRHpro  LAQELVVRLR SLQFDQREFV CLKFLVLFSS DVKNLENLQL VEGVQEQVNA 498

113PRO   ALLDYTMCNY PQQTEKFGQL LLRLPEIRAI SMQAEEYLYY KHLNGDVPYN 483
36pro    ALLDYTMCNY PQQTEKFRQL LLRLPEIRAI SMQAEEYLYY KHLNGDVPYN 311
hFTFpro  ALLDYTMCNY PQQTEKFGQL LLRLPEIRAI SMQAEEYLYY KHLNGDVPYN 488
mLRHpro  ALLDYTVCNY PQQTEKFGQL LLRLPEIRAI SKQAEDYLYY KHVNGDVPYN 548

113PRO   NLLIEMLHAK RA                                          495
36pro    NLLIEMLHAK RA                                          323
hFTFpro  NLLIEMLHAK RA                                          500
mLRHpro  NLLIEMLHAK RA                                          560
```

113PRO = SEQ ID NO:1
36PRO = SEQ ID NO:4
hFTFpro = SEQ ID NO:8
mLRHpro = SEQ ID NO:10

TABLE 7

```
105pro   MSSNSDTGDL QESLKHGLTP IG-------- ---------- ---AGLPDRH  29 hFTFpro  ---------- ---------- ---------- ---------- ---------- mLRHpro  MSASLDTGDF QEFLKHGLTA IASAPGSETR HSPKREEQLR EKRAGLPDRH  50

105pro   GSPIPARGRL VMLPKVETEA LGLARSHGEQ GQMPENMQVS QFKMVNYSYD  79 hFTFpro  ---------- -MLPKVETEA LGLARSHGEQ GQMPENMQVS QFKMVNYSYD  39 mLRHpro  RRPIPARSRL VMLPKVETEA PGLVRSHGEQ GQMPENMQVS QFKMVNYSYD 100

105pro   EDLEELCPVC GDKVSGYHYG LLTCESCKGF FKRTVQNNKR YTCIENQNCQ 129 hFTFpro  EDLEELCPVC GDKVSGYHYG LLTCESCKGF FKRTVQNNKR YTCIENQNCQ  89 mLRHpro  EDLEELCPVC GDKVSGYHYG LLTCESCKGF FKRTVQNQKR YTCIENQNCQ 150

105pro   IDKTQRKRCP YCRFQKCLSV GMKLEAVRAD RMRGGRNKFG PMYKRDRALK 179 hFTFpro  IDKTQRKRCP YCRFQKCLSV GMKLEAVRAD RMRGGRNKFG PMYKRDRALK 139 mLRHpro  IDKTQRKRCP YCRFKKCIDV GMKLEAVRAD RMRGGRNKFG PMYKRDRALK 200

105pro   QQKKALIRAN GLKLEAMSQV IQAMPSDLTI SSAIQNIHSA SKGLPLNHAA 229 hFTFpro  QQKKALIRAN GLKLEAMSQV IQAMPSDLTI SSAIQNIHSA SKGLPLNHAA 189 mLRHpro  QQKKALIRAN GLKLEAMSQV IQAMPSDLT- -SAIQNIHSA SKGLPLSHVA 248

105pro   LPPTDYDRSP FVTSPISMTM PPHGSLQGYQ TYGHFPSRAI KSEYPDPYTS 279 hFTFpro  LPPTDYDRSP FVTSPISMTM -LHGSLQGYQ TYGHFPSRAI KSEYPDPYTS 238 mLRHpro  LPPTDYDRSP FVTSPISMTM PPHSSLHGYQ PYGHFPSRAI KSEYPDPYSS 298

105pro   SPESIMGYSY MDSYQTSSPA SIPHLILELL KCEPDEPQVQ AKIMAYLQQE 329 hFTFpro  SPESIMGYSY MDSYQTSSPA SIPHLILELL KCEPDEPQVQ AKIMAYLQQE 288 mLRHpro  SPESMMGYSY MDGYQTNSPA SIPHLILELL KCEPDEPQVQ AKIMAYLQQE 348

105pro   QANRSKHEKL STFGLMCKMA DQTLFSIVEW ARSSIFFREL KVDDQMKLLQ 379 hFTFpro  QANRSKHEKL STFGLMCKMA DQTVFSIVEW ARSSIFFREL KVDDQMKLLQ 338 mLRHpro  QSNRNRQEKL SAFGLLCKMA DQTLFSIVEW ARSSIFFREL KVDDQMKLLQ 398

105pro   NCWSELLILD HIYRQVVHGK EGSIFLVTGQ QVDYSIIASQ AGATLNNLMS 429 hFTFpro  NCWSELLILD HIYRQVVHGK EGSIFLVTGQ QVDYSIIASQ AGATLNNLMS 388 mLRHpro  NCWSELLILD HIYRQVAHGK EGTIFLVTGE HVDYSTIISH TEVAFNNLMS 448

105pro   HAQELVAKLR SLQFDQREFV CLKFLVLFSL DVKNLENFQL VEGVQEQVNA 479 hFTFpro  HAQELVAKLR SLQFDQRHFV CLKFLVLFSL DVKNLENFQL VEGVQEQVNA 438 mLRHpro  LAQELVVRLR SLQFDQREFV CLKFLVLFSS DVKNLENLQL VEGVQEQVNA 498

105pro   ALLDYTMCNY PQQTEKFGQL LLRLPEIRAI SMQAEEYLYY KHLNGDVPYN 529 hFTFpro  ALLDYTMCNY PQQTEKFGQL LLRLPEIRAI SMQAEEYLYY KHLNGDVPYN 488 mLRHpro  ALLDYTVCNY PQQTEKFGQL LLRLPEIRAI SKQAEDYLYY KHVNGDVPYN 548

105pro   NLLIEMLHAK RA                                          541 hFTFpro  NLLIEMLHAK RA                                          500 mLRHPrQ  NLLIEMLHAK RA                                          560
```

05pro = SEQ ID NO:6
hFTFpro = SEQ ID NO:3
mLRHpro = SEQ ID NO:10

TABLE 8

```
113 = SEQ ID NO:1
hFTF = SEQ ID NO:7
```

| | | | | | | |
|---|---|---|---|---|---|---|
| 113  | ---------- | ---------- | ---------- | --------GA | AAAAAGTACA | 12 |
| hFTF | GAAACTGGAT | ACATGGTTTA | CAGCAGGTCA | CTAATGTTGG | AAAAAGTACA | 50 |
| 113  | GAGTCCAGGG | AAAAGACTTG | CTTGTAACTT | TATGAATTCT | GGATTTTTTT | 62 |
| hFTF | GAGTCCAGGG | AAA-GACTTG | CTTGTAACTT | TATGAATTCT | GGA---TTTT | 96 |
| 113  | TTTTCCTTTG | CTTTTTCTTA | ACTTTCACTA | AGGGTTACTG | TAGTCTGATG | 112 |
| hFTF | TTTTCCTTTG | CTTTTTCTTA | ACTTTCACTA | AGGGTTACTG | TAGTCTGATG | 146 |
| 113  | TGTCCTTCCC | AAGGCCACGA | AATTTGACAA | GCTGCACTTT | TCTTTTGCTC | 162 |
| hFTF | TGTCCTTCCC | AAGGCCACGA | AATTTGACAA | GCTGCACTTT | TCTTTTGCTC | 196 |
| 113  | AATGATTTCT | GCTTTAAGCC | AAAGAACTGC | CTATAATTTC | ACTAAGAATG | 212 |
| hFTF | AATGATTTCT | GCTTTAAGCC | AAAGAACTGC | CTATAATTTC | ACTAAGAATG | 246 |
| 113  | TCTTCTAATT | CAGATACTGG | GGATTTACAA | GAGTCTTTAA | AGCACGGACT | 262 |
| hFTF | TCTTCTAATT | CAGATACTGG | GGATTTACAA | GAGTCTTTAA | AGCACGGACT | 296 |
| 113  | TACACCTATT | ---------- | ---------- | ---------- | ---------- | 272 |
| hFTF | TACACCTATT | GGTGCTGGGC | TTCCGGACCG | ACACGGATCC | CCCATCCCGC | 346 |
| 113  | ---------- | ---------- | ---------- | ---------- | ---------- | 272 |
| hFTF | CCGCGGTCGC | CTTGTCATGC | TGCCCAAAGT | GGAGACGGAA | GCCCTGGGAC | 396 |
| 113  | ---------- | ---------- | ---------- | -------GTG | | 275 |
| hFTF | TGGCTCGATC | GCATGGGGAA | CAGGGCCAGA | TGCCGGAAAA | CATGCAAGTG | 446 |
| 113  | TCTCAATTTA | AAATGGTGAA | TTACTCCTAT | GATGAAGATC | TGGAAGAGCT | 325 |
| hFTF | TCTCAATTTA | AAATGGTGAA | TTACTCCTAT | GATGAAGATC | TGGAAGAGCT | 496 |
| 113  | TTGTCCCGTG | TGTGGAGATA | AAGTGTCTGG | GTACCATTAT | GGGCTCCTCA | 375 |
| hFTF | TTGTCCCGTG | TGTGGAGATA | AAGTGTCTGG | GTACCATTAT | GGGCTCCTCA | 546 |
| 113  | CCTGTGAAAG | CTGCAAGGGA | TTTTTTAAGC | GAACAGTCCA | AAATAATAAA | 425 |
| hFTF | CCTGTGAAAG | CTGCAAGGGA | TTTTTTAAGC | GAACAGTCCA | AAATAATAAA | 596 |
| 113  | AGGTACACAT | GTATAGAAAA | CCAGAACTGC | CAAATTGACA | AAACACAGAG | 475 |
| hFTF | AGGTACACAT | GTATAGAAAA | CCAGAACTGC | CAAATTGACA | AAACACAGAG | 646 |
| 113  | AAAGCGTTGT | CCTTACTGTC | GTTTTCAAAA | ATGTCTAAGT | GTTGGAATGA | 525 |
| hFTF | AAAGCGTTGT | CCTTACTGTC | GTTTTCAAAA | ATGTCTAAGT | GTTGGAATGA | 696 |
| 113  | AGCTAGAAGC | TGTAAGGGCC | GACCGAATGC | GTGGAGGAAG | GAATAAGTTT | 575 |
| hFTF | AGCTAGAAGC | TGTAAGGGCC | GACCGAATGC | GTGGAGGAAG | GAATAAGTTT | 746 |
| 113  | GGGCCAATGT | ACAAGAGAGA | CAGGGCCCTG | AAGCAACAGA | AAAAAGCCCT | 625 |
| hFTF | GGGCCAATGT | ACAAGAGAGA | CGGGGCCCTG | AAGCAACAGA | AAAAAGCCCT | 796 |
| 113  | CATCCGAGCC | AATGGACTTA | AGCTAGAAGC | CATGTCTCAG | GTGATCCAAG | 675 |
| hFTF | CATCCGAGCC | AATGGACTTA | AGCTAGAAGC | CATGTCTCAG | GTGATCCAAG | 846 |
| 113  | CTATGCCCTC | TGACCTGACC | ATTTCCTCTG | CAATTCAAAA | CATCCACTCT | 725 |
| hFTF | CTATGCCCTC | TGACCTGACC | ATTTCCTCTG | CAATTCAAAA | CATCCACTCT | 896 |
| 113  | GCCTCCAAAG | GCCTACCTCT | GAACCATGCT | GCCTTGCCTC | CTACAGACTA | 775 |
| hFTF | GCCTCCAAAG | GCCTACCTCT | GAACCATGCT | GCCTTGCCTC | CTACAGACTA | 946 |
| 113  | TGACAGAAGT | CCCTTTGTAA | CATCCCCCAT | TAGCATGACA | ATGCCCCCTC | 825 |
| hFTF | TGACAGAAGT | CCCTTTGTAA | CATCCCCCAT | TAGCATGACA | ATGC---TGC | 993 |
| 113  | ACGGCAGCCT | GCAAGGTTAC | CAAACATATG | GCCACTTTCC | TAGCCGGACC | 875 |
| hFTF | ACGGCAGCCT | GCAAGGTTAC | CAAACATATG | GCCACTTTCC | TAGCCGGGCC | 1043 |
| 113  | ATCAAGTCTG | AGTACCCAGA | CCCCTATACC | AGCTCACCCG | AGTCCATAAT | 925 |
| hFTF | ATCAAGTCTG | AGTACCCAGA | CCCCTATACC | AGCTCACCCG | AGTCCATAAT | 1093 |
| 113  | GGGCTATTCA | TATATGGATA | GTTACCAGAC | GAGCTCTCCA | GCAAGCATCC | 975 |
| hFTF | GGGCTATTCA | TATATGGATA | GTTACCAGAC | GAGCTCTCCA | GCAAGCATCC | 1143 |
| 113  | CACATCTGAT | ACTGGAACTT | TTGAAGTGTG | AGCCAGATGA | GCCTCAAGTC | 1025 |
| hFTF | CACATCTGAT | ACTGGAACTT | TTGAAGTGTG | AGCCAGATGA | GCCTCAAGTC | 1193 |
| 113  | CAGGCTAAAA | TCATGGCCTA | TTTGCAGCAA | GAGCAGGCTA | ACCGAAGCAA | 1075 |
| hFTF | CAGGCTAAAA | TCATGGCCTA | TTTGCAGCAA | GAGCAGGCTA | ACCGAAGCAA | 1243 |
| 113  | GCACGAAAAG | CTGAGCACCT | TGGGCTTAT | GTGCAAAATG | GCAGATCAAA | 1125 |
| hFTF | GCACGAAAAG | CTGAGCACCT | TGGGCTTAT | GTGCAAAATG | GCAGATCAAA | 1293 |
| 113  | CTCTCTTCTC | CATTGTCGAG | TGGGCCAGGA | GTAGTATCTT | CTTCAGAGAA | 1175 |
| hFTF | CTGTCTTCTC | CATTGTCGAG | TGGGCCAGGA | GTAGTATCTT | CTTCAGAGAA | 1343 |
| 113  | CTTAAGGTTG | ATGACCAAAT | GAAGCTGCTT | CAGAACTGCT | GGAGTGAGCT | 1225 |
| hFTF | CTTAAGGTTG | ATGACCAAAT | GAAGCTGCTT | CAGAACTGCT | GGAGTGAGCT | 1393 |
| 113  | CTTAATCCTC | GACCACATTT | ACCGACAAGT | GGTACATGGA | AAGGAAGGAT | 1275 |
| hFTF | CTTAATCCTC | GACCACATTT | ACCGACAAGT | GGTACATGGA | AAGGAAGGAT | 1443 |
| 113  | CCATCTTCCT | GGTTACTGGG | CAACAAGTGG | ACTATTCCAT | AATAGCATCA | 1325 |
| hFTF | CCATCTTCCT | GGTTACTGGG | CAACAAGTGG | ACTATTCCAT | AATAGCATCA | 1493 |
| 113  | CAAGCCGGAG | CCACCCTAAA | CAACCTCATG | AGTCATGCAC | AGGAGTTAGT | 1375 |
| hFTF | CAAGCCGGAG | CCACCCTCAA | CAACCTCATG | AGTCATGCAC | AGGAGTTAGT | 1543 |
| 113  | GGCAAAACTT | CGTTCTCTCC | AGTTTGATCA | ACGAGAGTTC | GTATGTCTGA | 1425 |
| hFTF | GGCAAAACTT | CGTTCTCTCC | AGTTTGATCA | ACGAGAGTTC | GTATGTCTGA | 1593 |
| 113  | AATTCTTGGT | GCTCTTTAGT | TTAGATGTCA | AAAACCTTGA | AAACTTCCAG | 1475 |
| hFTF | AATTCTTGGT | GCTCTTTAGT | TTAGATGTCA | AAAACCTTGA | AAACTTCCAG | 1643 |
| 113  | CTGGTAGAAG | GTGTCCAGGA | ACAAGTCAAT | GCCGCCCTGC | TGGACTACAC | 1525 |
| hFTF | CTGGTAGAAG | GTGTCCAGGA | ACAAGTCAAT | GCCGCCCTGC | TGGACTACAC | 1693 |
| 113  | AATGTGTAAC | TACCCGCAGC | AGACAGAGAA | ATTTGGACAG | CTACTTCTTC | 1575 |
| hFTF | AATGTGTAAC | TACCCGCAGC | AGACAGAGAA | ATTTGGACAG | CTACTTCTTC | 1743 |
| 113  | GACTACCCGA | AATCCGGGCC | ATCAGTATGC | AGGCTGAAGA | ATACCTCTAC | 1625 |
| hFTF | GACTACCCGA | AATCCGGGCC | ATCAGTATGC | AGGCTGAAGA | ATACCTCTAC | 1793 |
| 113  | TACAAGCACC | TGAACGGGGA | TGTGCCCTAT | AATAACCTTC | TCATTGAAAT | 1675 |
| hFTF | TACAAGCACC | TGAATGGGGA | TGTGCCCTAT | AATAACCTTC | TCATTGAAAT | 1843 |
| 113  | GTTGCATGCC | AAAAGAGCAT | AAGTTACAAC | CCCTAGGAGC | TCTGCTTTCA | 1725 |
| hFTF | GTTGCATGCC | AAAAGAGCAT | AAGTTACAAC | CCCTAGGAGC | TCTGCTTTCA | 1893 |

TABLE 8-continued

```
113 = SEQ ID NO:1
hFTF = SEQ ID NO:7
```

| | | | | | | |
|---|---|---|---|---|---|---|
| 113 | AAACAAAAAG | AGATTGGGGG | AGTGGGGAGG | GGGAAGAAGA | ACAGGAAGAA | 1775 |
| hFTF | AAACAAAAAG | AGATTGGGGG | AGTGGGGAGG | GGGAAGAAGA | ACAGGAAGAA | 1943 |
| 113 | AAAAAGTACT | CTGAACTGCT | CCAAGCAACG | CTAATTAAAA | ACTTGCTTTA | 1825 |
| hFTP | AAAAAGTACT | CTGAACTGCT | CCAAGTAACG | CTAATTAAAA | ACTTGCTTTA | 1993 |
| 113 | AAGATATTGA | ATTTAAAAAG | GCATAATAAT | CAAATACTTA | ATAGCAAATA | 1875 |
| hFTF | AAGATATTGA | ATTTAAAAAG | GCATAATAAT | CAAATACT-A | ATAGCAAATA | 2042 |
| 113 | AATGATGTAT | CAGGGTATTT | GTATTGCAAA | CTGTGAATCA | AAGGCTTCAC | 1925 |
| hFTF | AATGATGTAT | CAGGGTATTT | GTATTGCAAA | CTGTGAATCA | AA-GCTTCAC | 2091 |
| 113 | AGCCCCAGAG | GATTCCATAT | AAAAGACATT | GTAATGGAGT | GGATTGAACT | 1975 |
| hFTF | AGCCCCAGAG | GATTCCATAT | AAAAGACATT | GTAATGGAGT | GGATTGAACT | 2141 |
| 113 | CACAGATGGA | TACCAACACG | GTCAGAAGAA | AAACGGACAG | AACGGTTCTT | 2025 |
| hFTF | CACAGATGGA | TACCAACACG | GTCAGAAGAA | AAACGGACAG | AACGGTTCTT | 2191 |
| 113 | GTATATTTAA | ACTGATCTCC | ACTATGAAGA | AATTTAGGAA | CTAATCTTAT | 2075 |
| hFTF | GTATATTTAA | ACTGATCTCC | ACTATGAAGA | AATTTAGGAA | CTAATCTTAT | 2241 |
| 113 | TAATTAGGCT | TATACAGCGG | GGGATTGAG | CTTACAGGAT | TCCTCCATGG | 2125 |
| hFTF | TAATTAGGCT | TATACAGCGG | GG-ATTTGAG | CTTACAGGAT | TCCTCCATGG | 2290 |
| 113 | TAAAGCTGAA | CTGAAACAAT | TCTCAAGAAT | GCATCAGCTG | TACCTACAAT | 2175 |
| hFTF | TAAAGCTGAA | CTGAAACAAT | TCTCAAGAAT | GCATCAGCTG | ---------- | 2330 |
| 113 | AGCCCCTCCC | TCTTCCTTTG | AAGGCCCGAG | CACCTCTGCC | CTGTGGTCAC | 2225 |
| hFTF | ---------- | ---------- | ---------- | ---------- | ---------- | 2330 |
| 113 | CGAATCTGTA | CTAAGGACCT | GTGTTCAGCC | ACACCCAGTG | GTAGCTCCAC | 2275 |
| hFTF | ---------- | ---------- | ---------- | ---------- | ---------- | 2330 |
| 113 | CAAATCATGA | ACAGCCTAAT | TTTGAGTGTC | TGTGTCTTAG | ACCTGCAAAC | 2325 |
| hFTF | ---------- | ---------- | ---------- | ---------- | ---------- | 2330 |
| 113 | AGCTAATAGG | AAATTCTATT | AATATGTTAG | CTTGCCATTT | TAAATATGTT | 2375 |
| hFTF | ---------- | ---------- | ---------- | ---------- | ---------- | 2330 |
| 113 | CTGAGGGTTG | TTTTGTCTCG | TGTTCATGAT | GTTAAGAAAA | TGCAGGCAGT | 2425 |
| hFTF | ---------- | ---------- | ---------- | ---------- | ---------- | 2330 |
| 113 | ATCCCTCATC | TTATGTAAGT | GTGAATTAAT | ATTAAGGGAA | ATGACTACAA | 2475 |
| hFTF | ---------- | ---------- | ---------- | ---------- | ---------- | 2330 |
| 113 | ACTTTCAAAG | CAAATGCTCC | ATAGCTAAAG | CAACTTAGAC | CTTATTTCTG | 2525 |
| hFTF | ---------- | ---------- | ---------- | ---------- | ---------- | 2330 |
| 113 | CTACTGTTGC | TGAAATGTGG | CTTTGGCATT | GTTGGATTTC | ATAAAAAATT | 2575 |
| hFTF | ---------- | ---------- | ---------- | ---------- | ---------- | 2330 |
| 113 | TCTGGCAGGA | AGTCTTGTTA | GTATACATCA | GTCTTTTTCA | TCATCCAAGT | 2625 |
| hFTF | ---------- | ---------- | ---------- | ---------- | ---------- | 2330 |
| 113 | TTGTAGTTCA | TTTAAAAATA | CAACATTAAA | CACATTTTGC | TAGGATGTCA | 2675 |
| hFTF | ---------- | ---------- | ---------- | ---------- | ---------- | 2330 |
| 113 | AATAGTCACA | GTTCTAAGTA | GTTGGAAACA | AAATTGACGC | ATGTTAATCT | 2725 |
| hFTF | ---------- | ---------- | ---------- | ---------- | ---------- | 2330 |
| 113 | ATGCAAAGAG | AAAGGAAAGG | ATGAGGTGAT | GTATTGACTC | AAGGTTCATT | 2775 |
| hFTF | ---------- | ---------- | ---------- | ---------- | ---------- | 2330 |
| 113 | CTTGCTGCAA | TTGAACATCC | TCAAGAGTTG | GGATGGAAAT | GGTGATTTTT | 2825 |
| hFTF | ---------- | ---------- | ---------- | ---------- | ---------- | 2330 |
| 113 | ACATGTGTCC | TGGAAAGATA | TTAAAGTAAT | TCAAATCTTC | CCCAAAGGGG | 2875 |
| hFTF | ---------- | ---------- | ---------- | ---------- | ---------- | 2330 |
| 113 | AAAGGAAGAG | AGTGATACTG | ACCTTTTTAA | GTCATAGACC | AAAGTCTGCT | 2925 |
| hFTF | ---------- | ---------- | ---------- | ---------- | ---------- | 2330 |
| 113 | GTAGAACAAA | TATGGGAGGA | CAAAGAATCG | CAAATTCTTC | AAATGACTAT | 2975 |
| hFTF | ---------- | ---------- | ---------- | ---------- | ---------- | 2330 |
| 113 | TATCAGTATT | ATTAACATGC | GATGCCACAG | GTATGAAAGT | CTTGCCTTAT | 3025 |
| hFTF | ---------- | ---------- | ---------- | ---------- | ---------- | 2330 |
| 113 | TTCACAATTT | TAAAAGGTAG | CTGTGCAGAT | GTGGATCAAC | ATTTGTTTAA | 3075 |
| hFTF | ---------- | ---------- | ---------- | ---------- | ---------- | 2330 |
| 113 | AATAAAGTAT | TAATACTTTA | AAGTCAAAAA | AAAAAAAAAA | | 3115 |
| hFTF | ---------- | ---------- | ---------- | ---------- | | 2330 |

What is claimed is:

1. A recombinant nucleic acid comprising a strand of sequence selected from the group consisting of SEQ ID NO:1, SEQ ID NO:3, and SEQ ID NO:5, wherein said strand is flanked by fewer than 2 kb of native flanking sequence.

2. A recombinant nucleic acid comprising a coding region encoding a polypeptide which comprises a sequence selected from the group consisting of SEQ ID NO:2, SEQ ID NO:4, and SEQ ID NO:6, wherein said coding region is flanked by fewer than 2 kb of native flanking sequence.

3. An isolated cell comprising the nucleic acid of claim 2.

4. A method of making a CPF polypeptide, said method comprising the steps:
   a) introducing the nucleic acid according to claim 2 into a host cell or cellular extract;
   b) incubating said host cell or cellular extract resulting from step (a) under conditions whereby said nucleic acid is expressed as a transcript and said transcript is expressed as a translation product comprising said polypeptide; and
   c) isolating said translation product.

5. A method of screening for an agent which modulates the interaction of a CPF polypeptide to a binding target, said method comprising the steps of:
   a) translating the nucleic acid according to claim 2 to produce the CPF polypeptide;
   b) incubating in vitro or in culture a mixture comprising:
      the CPF polypeptide,
      the binding target of said polypeptide, and
      a candidate agent,
   under conditions whereby, but for the presence of said candidate agent, said polypeptide specifically binds said binding target at a reference affinity; and
   c) detecting the binding affinity of said polypeptide to said binding target in the mixture resulting from step (b) to determine an agent-biased affinity, wherein a difference between the agent-biased affinity and the reference affinity indicates that said candidate agent is an agent that modulates the binding of said polypeptide to said binding target.

* * * * *

SEQUENCE LISTING

<160> NUMBER OF SEQ ID NOS: 30

<210> SEQ ID NO 1
<211> LENGTH: 3115
<212> TYPE: DNA
<213> ORGANISM: human
<220> FEATURE:
<221> NAME/KEY: CDS
<222> LOCATION: (210)..(1694)

<400> SEQUENCE: 1

-continued

```
gaaaaaagta cagagtccag ggaaaagact tgcttgtaac tttatgaatt ctggattttt        60 tttttttcctt tgctttttct taactttcac taagggttac tgtagtctga tgtgtccttc      120
ccaaggccac gaaatttgac aagctgcact tttcttttgc tcaatgattt ctgctttaag      180
ccaaagaact gcctataatt tcactaaga atg tct tct aat tca gat act ggg        233
                                Met Ser Ser Asn Ser Asp Thr Gly
                                  1               5 gat tta caa gag tct tta aag cac gga ctt aca cct att gtg tct caa        281
Asp Leu Gln Glu Ser Leu Lys His Gly Leu Thr Pro Ile Val Ser Gln
         10              15                  20 ttt aaa atg gtg aat tac tcc tat gat gaa gat ctg gaa gag ctt tgt        329
Phe Lys Met Val Asn Tyr Ser Tyr Asp Glu Asp Leu Glu Glu Leu Cys
 25              30                  35                  40 ccc gtg tgt gga gat aaa gtg tct ggg tac cat tat ggg ctc ctc acc        377
Pro Val Cys Gly Asp Lys Val Ser Gly Tyr His Tyr Gly Leu Leu Thr
                 45                  50                  55 tgt gaa agc tgc aag gga ttt ttt aag cga aca gtc caa aat aat aaa        425
Cys Glu Ser Cys Lys Gly Phe Phe Lys Arg Thr Val Gln Asn Asn Lys
             60                  65                  70 agg tac aca tgt ata gaa aac cag aac tgc caa att gac aaa aca cag        473
Arg Tyr Thr Cys Ile Glu Asn Gln Asn Cys Gln Ile Asp Lys Thr Gln
                 75                  80                  85 aga aag cgt tgt cct tac tgt cgt ttt caa aaa tgt cta agt gtt gga        521
Arg Lys Arg Cys Pro Tyr Cys Arg Phe Gln Lys Cys Leu Ser Val Gly
         90                  95                 100 atg aag cta gaa gct gta agg gcc gac cga atg cgt gga gga agg aat        569
Met Lys Leu Glu Ala Val Arg Ala Asp Arg Met Arg Gly Gly Arg Asn
105                 110                 115                 120 aag ttt ggg cca atg tac aag aga gac agg gcc ctg aag caa cag aaa        617
Lys Phe Gly Pro Met Tyr Lys Arg Asp Arg Ala Leu Lys Gln Gln Lys
                125                 130                 135 aaa gcc ctc atc cga gcc aat gga ctt aag cta gaa gcc atg tct cag        665
Lys Ala Leu Ile Arg Ala Asn Gly Leu Lys Leu Glu Ala Met Ser Gln
            140                 145                 150 gtg atc caa gct atg ccc tct gac ctg acc att tcc tct gca att caa        713
Val Ile Gln Ala Met Pro Ser Asp Leu Thr Ile Ser Ser Ala Ile Gln
            155                 160                 165 aac atc cac tct gcc tcc aaa ggc cta cct ctg aac cat gct gcc ttg        761
Asn Ile His Ser Ala Ser Lys Gly Leu Pro Leu Asn His Ala Ala Leu
        170                 175                 180 cct cct aca gac tat gac aga agt ccc ttt gta aca tcc ccc att agc        809
Pro Pro Thr Asp Tyr Asp Arg Ser Pro Phe Val Thr Ser Pro Ile Ser
185                 190                 195                 200 atg aca atg ccc cct cac ggc agc ctg caa ggt tac caa aca tat ggc        857
Met Thr Met Pro Pro His Gly Ser Leu Gln Gly Tyr Gln Thr Tyr Gly
                205                 210                 215 cac ttt cct agc cgg gcc atc aag tct gag tac cca gac ccc tat acc        905
His Phe Pro Ser Arg Ala Ile Lys Ser Glu Tyr Pro Asp Pro Tyr Thr
            220                 225                 230 agc tca ccc gag tcc ata atg ggc tat tca tat atg gat agt tac cag        953
Ser Ser Pro Glu Ser Ile Met Gly Tyr Ser Tyr Met Asp Ser Tyr Gln
        235                 240                 245 acg agc tct cca gca agc atc cca cat ctg ata ctg gaa ctt ttg aag       1001
Thr Ser Ser Pro Ala Ser Ile Pro His Leu Ile Leu Glu Leu Leu Lys
250                 255                 260 tgt gag cca gat gag cct caa gtc cag gct aaa atc atg gcc tat ttg       1049
Cys Glu Pro Asp Glu Pro Gln Val Gln Ala Lys Ile Met Ala Tyr Leu
265                 270                 275                 280 cag caa gag cag gct aac cga agc aag cac gaa aag ctg agc acc ttt       1097
Gln Gln Glu Gln Ala Asn Arg Ser Lys His Glu Lys Leu Ser Thr Phe
```

-continued

|  |  |  |  |
|---|---|---|---|
| | 285 | 290 | 295 |
| ggg ctt atg tgc aaa atg gca gat caa act ctc ttc tcc att gtc gag<br>Gly Leu Met Cys Lys Met Ala Asp Gln Thr Leu Phe Ser Ile Val Glu<br>300                    305                     310 | | | 1145 |
| tgg gcc agg agt agt atc ttc ttc aga gaa ctt aag gtt gat gac caa<br>Trp Ala Arg Ser Ser Ile Phe Phe Arg Glu Leu Lys Val Asp Asp Gln<br>315                   320                    325 | | | 1193 |
| atg aag ctg ctt cag aac tgc tgg agt gag ctc tta atc ctc gac cac<br>Met Lys Leu Leu Gln Asn Cys Trp Ser Glu Leu Leu Ile Leu Asp His<br>330                   335                  340 | | | 1241 |
| att tac cga caa gtg gta cat gga aag gaa gga tcc atc ttc ctg gtt<br>Ile Tyr Arg Gln Val Val His Gly Lys Glu Gly Ser Ile Phe Leu Val<br>345                 350                   355                 360 | | | 1289 |
| act ggg caa caa gtg gac tat tcc ata ata gca tca caa gcc gga gcc<br>Thr Gly Gln Gln Val Asp Tyr Ser Ile Ile Ala Ser Gln Ala Gly Ala<br>365                   370                  375 | | | 1337 |
| acc ctc aac aac ctc atg agt cat gca cag gag tta gtg gca aaa ctt<br>Thr Leu Asn Asn Leu Met Ser His Ala Gln Glu Leu Val Ala Lys Leu<br>380                   385                  390 | | | 1385 |
| cgt tct ctc cag ttt gat caa cga gag ttc gta tgt ctg aaa ttc ttg<br>Arg Ser Leu Gln Phe Asp Gln Arg Glu Phe Val Cys Leu Lys Phe Leu<br>395                   400                  405 | | | 1433 |
| gtg ctc ttt agt tta gat gtc aaa aac ctt gaa aac ttc cag ctg gta<br>Val Leu Phe Ser Leu Asp Val Lys Asn Leu Glu Asn Phe Gln Leu Val<br>410                   415                  420 | | | 1481 |
| gaa ggt gtc cag gaa caa gtc aat gcc gcc ctg ctg gac tac aca atg<br>Glu Gly Val Gln Glu Gln Val Asn Ala Ala Leu Leu Asp Tyr Thr Met<br>425                 430                   435                 440 | | | 1529 |
| tgt aac tac ccg cag cag aca gag aaa ttt gga cag cta ctt ctt cga<br>Cys Asn Tyr Pro Gln Gln Thr Glu Lys Phe Gly Gln Leu Leu Leu Arg<br>445                 450                  455 | | | 1577 |
| cta ccc gaa atc cgg gcc atc agt atg cag gct gaa gaa tac ctc tac<br>Leu Pro Glu Ile Arg Ala Ile Ser Met Gln Ala Glu Glu Tyr Leu Tyr<br>460                   465                  470 | | | 1625 |
| tac aag cac ctg aac ggg gat gtg ccc tat aat aac ctt ctc att gaa<br>Tyr Lys His Leu Asn Gly Asp Val Pro Tyr Asn Asn Leu Leu Ile Glu<br>475                 480                   485 | | | 1673 |
| atg ttg cat gcc aaa aga gca taagttacaa cccctaggag ctctgctttc<br>Met Leu His Ala Lys Arg Ala<br>490                   495 | | | 1724 |
| aaaacaaaaa gagattgggg gagtggggag ggggaagaag aacaggaaga aaaaaagtac | | | 1784 |
| tctgaactgc tccaagcaac gctaattaaa aacttgcttt aaagatattg aatttaaaaa | | | 1844 |
| ggcataataa tcaaatactt aatagcaaat aaatgatgta tcagggtatt tgtattgcaa | | | 1904 |
| actgtgaatc aaaggcttca cagccccaga ggattccata taaaagacat tgtaatggag | | | 1964 |
| tggattgaac tcacagatgg ataccaacac ggtcagaaga aaaacggaca gaacggttct | | | 2024 |
| tgtatattta aactgatctc cactatgaag aaatttagga actaatctta ttaattaggc | | | 2084 |
| ttatacagcg ggggatttga gcttacagga ttcctccatg gtaaagctga actgaaacaa | | | 2144 |
| ttctcaagaa tgcatcagct gtacctacaa tagcccctcc ctcttccttt gaaggcccga | | | 2204 |
| gcacctctgc cctgtggtca ccgaatctgt actaaggacc tgtgttcagc cacacccagt | | | 2264 |
| ggtagctcca ccaaatcatg aacagcctaa ttttgagtgt ctgtgtctta gacctgcaaa | | | 2324 |
| cagctaatag gaaattctat taatatgtta gcttgccatt ttaaatatgt tctgagggtt | | | 2384 |
| gttttgtctc gtgttcatga tgttaagaaa atgcaggcag tatccctcat cttatgtaag | | | 2444 |
| tgtgaattaa tattaaggga aatgactaca aactttcaaa gcaaatgctc catagctaaa | | | 2504 |

-continued

```
gcaacttaga ccttatttct gctactgttg ctgaaatgtg gctttggcat tgttggattt     2564
cataaaaaat ttctggcagg aagtcttgtt agtatacatc agtcttttc atcatccaag      2624 tttgtagttc atttaaaaat acaacattaa acacattttg ctaggatgtc aaatagtcac    2684
agttctaagt agttggaaac aaaattgacg catgttaatc tatgcaaaga gaaggaaag     2744 gatgaggtga tgtattgact caaggttcat tcttgctgca attgaacatc ctcaagagtt    2804
gggatggaaa tggtgatttt tacatgtgtc ctggaaagat attaaagtaa ttcaaatctt    2864
ccccaaaggg gaaaggaaga gagtgatact gaccttttta agtcatagac caaagtctgc   2924
tgtagaacaa atatgggagg acaaagaatc gcaaattctt caaatgacta ttatcagtat   2984
tattaacatg cgatgccaca ggtatgaaag tcttgcctta tttcacaatt ttaaaaggta   3044
gctgtgcaga tgtggatcaa catttgttta aataaagta ttaatacttt aaagtcaaaa    3104
aaaaaaaaaa a                                                         3115
```

<210> SEQ ID NO 2
<211> LENGTH: 495
<212> TYPE: PRT
<213> ORGANISM: human

<400> SEQUENCE: 2

```
Met Ser Ser Asn Ser Asp Thr Gly Asp Leu Gln Glu Ser Leu Lys His
  1               5                  10                  15

Gly Leu Thr Pro Ile Val Ser Gln Phe Lys Met Val Asn Tyr Ser Tyr
                 20                  25                  30

Asp Glu Asp Leu Glu Glu Leu Cys Pro Val Cys Gly Asp Lys Val Ser
             35                  40                  45

Gly Tyr His Tyr Gly Leu Leu Thr Cys Glu Ser Cys Lys Gly Phe Phe
         50                  55                  60

Lys Arg Thr Val Gln Asn Asn Lys Arg Tyr Thr Cys Ile Glu Asn Gln
 65                  70                  75                  80

Asn Cys Gln Ile Asp Lys Thr Gln Arg Lys Arg Cys Pro Tyr Cys Arg
                 85                  90                  95

Phe Gln Lys Cys Leu Ser Val Gly Met Lys Leu Glu Ala Val Arg Ala
                100                 105                 110

Asp Arg Met Arg Gly Gly Arg Asn Lys Phe Gly Pro Met Tyr Lys Arg
            115                 120                 125

Asp Arg Ala Leu Lys Gln Gln Lys Lys Ala Leu Ile Arg Ala Asn Gly
        130                 135                 140

Leu Lys Leu Glu Ala Met Ser Gln Val Ile Gln Ala Met Pro Ser Asp
145                 150                 155                 160

Leu Thr Ile Ser Ser Ala Ile Gln Asn Ile His Ser Ala Ser Lys Gly
                165                 170                 175

Leu Pro Leu Asn His Ala Ala Leu Pro Pro Thr Asp Tyr Asp Arg Ser
            180                 185                 190

Pro Phe Val Thr Ser Pro Ile Ser Met Thr Met Pro Pro His Gly Ser
        195                 200                 205

Leu Gln Gly Tyr Gln Thr Tyr Gly His Phe Pro Ser Arg Ala Ile Lys
    210                 215                 220

Ser Glu Tyr Pro Asp Pro Tyr Thr Ser Ser Pro Glu Ser Ile Met Gly
225                 230                 235                 240

Tyr Ser Tyr Met Asp Ser Tyr Gln Thr Ser Ser Pro Ala Ser Ile Pro
                245                 250                 255

His Leu Ile Leu Glu Leu Leu Lys Cys Glu Pro Asp Glu Pro Gln Val
            260                 265                 270
```

```
Gln Ala Lys Ile Met Ala Tyr Leu Gln Gln Glu Gln Ala Asn Arg Ser
            275                 280                 285

Lys His Glu Lys Leu Ser Thr Phe Gly Leu Met Cys Lys Met Ala Asp
        290                 295                 300

Gln Thr Leu Phe Ser Ile Val Glu Trp Ala Arg Ser Ser Ile Phe Phe
305                 310                 315                 320

Arg Glu Leu Lys Val Asp Asp Gln Met Lys Leu Leu Gln Asn Cys Trp
                325                 330                 335

Ser Glu Leu Leu Ile Leu Asp His Ile Tyr Arg Gln Val Val His Gly
            340                 345                 350

Lys Glu Gly Ser Ile Phe Leu Val Thr Gly Gln Gln Val Asp Tyr Ser
        355                 360                 365

Ile Ile Ala Ser Gln Ala Gly Ala Thr Leu Asn Asn Leu Met Ser His
370                 375                 380

Ala Gln Glu Leu Val Ala Lys Leu Arg Ser Leu Gln Phe Asp Gln Arg
385                 390                 395                 400

Glu Phe Val Cys Leu Lys Phe Leu Val Leu Phe Ser Leu Asp Val Lys
                405                 410                 415

Asn Leu Glu Asn Phe Gln Leu Val Glu Gly Val Gln Glu Gln Val Asn
            420                 425                 430

Ala Ala Leu Leu Asp Tyr Thr Met Cys Asn Tyr Pro Gln Gln Thr Glu
        435                 440                 445

Lys Phe Gly Gln Leu Leu Leu Arg Leu Pro Glu Ile Arg Ala Ile Ser
    450                 455                 460

Met Gln Ala Glu Glu Tyr Leu Tyr Tyr Lys His Leu Asn Gly Asp Val
465                 470                 475                 480

Pro Tyr Asn Asn Leu Leu Ile Glu Met Leu His Ala Lys Arg Ala
                485                 490                 495

<210> SEQ ID NO 3
<211> LENGTH: 1245
<212> TYPE: DNA
<213> ORGANISM: human
<220> FEATURE:
<221> NAME/KEY: CDS
<222> LOCATION: (202)..(1170)

<400> SEQUENCE: 3
cggccgcgtc gacggaaaga cttgcttgta actttatgaa ttctggattt ttttttttcc      60 tttgctttt  cttaactttc actaagggtt actgtagtct gatgtgtcct tcccaaggcc     120
acgaaatttg acaagctgca cttttctttt gctcaatgat ttctgcttta agccaaagaa     180
ctgcctataa tttcactaag a atg tct tct aat tca gat act ggg gat tta      231
                         Met Ser Ser Asn Ser Asp Thr Gly Asp Leu
                          1               5                   10 caa gag tct tta aag cac gga ctt aca cct att gtg tct caa ttt aaa      279
Gln Glu Ser Leu Lys His Gly Leu Thr Pro Ile Val Ser Gln Phe Lys
            15                  20                  25 atg gtg aat tac tcc tat gat gaa gat ctg gaa gag ctt tgt ccc gtg      327
Met Val Asn Tyr Ser Tyr Asp Glu Asp Leu Glu Glu Leu Cys Pro Val
        30                  35                  40 tgt gga gat aaa gtg tct ggg tac cat tat ggg ctc ctc acc tgt gaa      375
Cys Gly Asp Lys Val Ser Gly Tyr His Tyr Gly Leu Leu Thr Cys Glu
    45                  50                  55 agc tgc aag gga ttt ttt aag cga aca gtc caa aat aat aaa agg tac      423
Ser Cys Lys Gly Phe Phe Lys Arg Thr Val Gln Asn Asn Lys Arg Tyr
60                  65                  70
```

| | | |
|---|---|---|
| aca tgt ata gaa aac cag aac tgc caa att gac aaa aca cag aga aag<br>Thr Cys Ile Glu Asn Gln Asn Cys Gln Ile Asp Lys Thr Gln Arg Lys<br>75                    80                  85                  90 | 471 |

```
aca tgt ata gaa aac cag aac tgc caa att gac aaa aca cag aga aag      471
Thr Cys Ile Glu Asn Gln Asn Cys Gln Ile Asp Lys Thr Gln Arg Lys
 75                  80                  85                  90 cgt tgt cct tac tgt cgt ttt caa aaa tgt cta agt gtt gga atg aag      519
Arg Cys Pro Tyr Cys Arg Phe Gln Lys Cys Leu Ser Val Gly Met Lys
                 95                 100                 105 cta gaa gct gta agg gcc gac cga atg cgt gga gga agg aat aag ttt      567
Leu Glu Ala Val Arg Ala Asp Arg Met Arg Gly Gly Arg Asn Lys Phe
            110                 115                 120 ggg cca atg tac aag aga gac agg gcc ctg aag caa cag aaa aaa gcc      615
Gly Pro Met Tyr Lys Arg Asp Arg Ala Leu Lys Gln Gln Lys Lys Ala
        125                 130                 135 ctc atc cga gcc aat gga ctt aag cta gaa gcc atg tct cag gtt gat      663
Leu Ile Arg Ala Asn Gly Leu Lys Leu Glu Ala Met Ser Gln Val Asp
    140                 145                 150 gac caa atg aag ctg ctt cag aac tgc tgg agt gag ctc tta atc ctc      711
Asp Gln Met Lys Leu Leu Gln Asn Cys Trp Ser Glu Leu Leu Ile Leu
155                 160                 165                 170 gac cac att tac cga caa gtg gta cat gga aag gaa gga tcc atc ttc      759
Asp His Ile Tyr Arg Gln Val Val His Gly Lys Glu Gly Ser Ile Phe
                175                 180                 185 ctg gtt act ggg caa caa gtg gac tat tcc ata ata gca tca caa gcc      807
Leu Val Thr Gly Gln Gln Val Asp Tyr Ser Ile Ile Ala Ser Gln Ala
            190                 195                 200 gga gcc acc ctc aac aac ctc atg agt cat gca cag gag tta gtg gca      855
Gly Ala Thr Leu Asn Asn Leu Met Ser His Ala Gln Glu Leu Val Ala
        205                 210                 215 aaa ctt cgt tct ctc cag ttt gat caa cga gag ttc gta tgt ctg aaa      903
Lys Leu Arg Ser Leu Gln Phe Asp Gln Arg Glu Phe Val Cys Leu Lys
    220                 225                 230 ttc ttg gtg ctc ttt agt tta gat gtc aaa aac ctt gaa aac ttc cag      951
Phe Leu Val Leu Phe Ser Leu Asp Val Lys Asn Leu Glu Asn Phe Gln
235                 240                 245                 250 ctg gta gaa ggt gtc cag gaa caa gtc aat gcc gcc ctg ctg gac tac      999
Leu Val Glu Gly Val Gln Glu Gln Val Asn Ala Ala Leu Leu Asp Tyr
                255                 260                 265 aca atg tgt aac tac ccg cag cag aca gag aaa ttt cga cag cta ctt     1047
Thr Met Cys Asn Tyr Pro Gln Gln Thr Glu Lys Phe Arg Gln Leu Leu
            270                 275                 280 ctt cga cta ccc gaa atc cgg gcc atc agt atg cag gct gaa gaa tac     1095
Leu Arg Leu Pro Glu Ile Arg Ala Ile Ser Met Gln Ala Glu Glu Tyr
        285                 290                 295 ctc tac tac aag cac ctg aac ggg gat gtg ccc tat aat aac ctt ctc     1143
Leu Tyr Tyr Lys His Leu Asn Gly Asp Val Pro Tyr Asn Asn Leu Leu
    300                 305                 310 att gaa atg ttg cat gcc aaa aga gca taagttacaa ccctaggag            1190
Ile Glu Met Leu His Ala Lys Arg Ala
315                 320 ctctgctttc aaacaaaaa gagattgggg gagtggggag ggggaagaag aacag         1245

<210> SEQ ID NO 4
<211> LENGTH: 323
<212> TYPE: PRT
<213> ORGANISM: human

<400> SEQUENCE: 4

Met Ser Ser Asn Ser Asp Thr Gly Asp Leu Gln Glu Ser Leu Lys His
  1               5                  10                  15

Gly Leu Thr Pro Ile Val Ser Gln Phe Lys Met Val Asn Tyr Ser Tyr
             20                  25                  30
```

-continued

```
Asp Glu Asp Leu Glu Glu Leu Cys Pro Val Cys Gly Asp Lys Val Ser
             35                  40                  45

Gly Tyr His Tyr Gly Leu Leu Thr Cys Glu Ser Cys Lys Gly Phe Phe
 50                  55                  60

Lys Arg Thr Val Gln Asn Asn Lys Arg Tyr Thr Cys Ile Glu Asn Gln
 65                  70                  75                  80

Asn Cys Gln Ile Asp Lys Thr Gln Arg Lys Arg Cys Pro Tyr Cys Arg
             85                  90                  95

Phe Gln Lys Cys Leu Ser Val Gly Met Lys Leu Glu Ala Val Arg Ala
            100                 105                 110

Asp Arg Met Arg Gly Gly Arg Asn Lys Phe Gly Pro Met Tyr Lys Arg
            115                 120                 125

Asp Arg Ala Leu Lys Gln Gln Lys Lys Ala Leu Ile Arg Ala Asn Gly
130                 135                 140

Leu Lys Leu Glu Ala Met Ser Gln Val Asp Asp Gln Met Lys Leu Leu
145                 150                 155                 160

Gln Asn Cys Trp Ser Glu Leu Leu Ile Leu Asp His Ile Tyr Arg Gln
                165                 170                 175

Val Val His Gly Lys Glu Gly Ser Ile Phe Leu Val Thr Gly Gln Gln
            180                 185                 190

Val Asp Tyr Ser Ile Ile Ala Ser Gln Ala Gly Ala Thr Leu Asn Asn
            195                 200                 205

Leu Met Ser His Ala Gln Glu Leu Val Ala Lys Leu Arg Ser Leu Gln
210                 215                 220

Phe Asp Gln Arg Glu Phe Val Cys Leu Lys Phe Leu Val Leu Phe Ser
225                 230                 235                 240

Leu Asp Val Lys Asn Leu Glu Asn Phe Gln Leu Val Glu Gly Val Gln
                245                 250                 255

Glu Gln Val Asn Ala Ala Leu Leu Asp Tyr Thr Met Cys Asn Tyr Pro
            260                 265                 270

Gln Gln Thr Glu Lys Phe Arg Gln Leu Leu Leu Arg Leu Pro Glu Ile
            275                 280                 285

Arg Ala Ile Ser Met Gln Ala Glu Glu Tyr Leu Tyr Tyr Lys His Leu
290                 295                 300

Asn Gly Asp Val Pro Tyr Asn Asn Leu Leu Ile Glu Met Leu His Ala
305                 310                 315                 320

Lys Arg Ala
```

<210> SEQ ID NO 5
<211> LENGTH: 3251
<212> TYPE: DNA
<213> ORGANISM: human
<220> FEATURE:
<221> NAME/KEY: CDS
<222> LOCATION: (208)..(1830)

<400> SEQUENCE: 5

```
cgcggccgcg tcgaccaggg aaaagacttg cttgtaactt tatgaattct ggatttttt      60 ttttcctttg cttttttctta actttcacta agggttactg tagtctgatg tgtccttccc    120
aaggccacga aatttgacaa gctgcacttt tcttttgctc aatgatttct gctttaagcc    180
aaagaactgc ctataatttc actaaga atg tct tct aat tca gat act ggg gat    234
                                 Met Ser Ser Asn Ser Asp Thr Gly Asp
                                  1               5 tta caa gag tct tta aag cac gga ctt aca cct att ggt gct ggg ctt     282
Leu Gln Glu Ser Leu Lys His Gly Leu Thr Pro Ile Gly Ala Gly Leu
 10                  15                  20                  25
```

```
ccg gac cga cac gga tcc ccc atc ccc gcc cgc ggt cgc ctt gtc atg      330
Pro Asp Arg His Gly Ser Pro Ile Pro Ala Arg Gly Arg Leu Val Met
             30                  35                  40 ctg ccc aaa gtg gag acg gaa gcc ctg gga ctg gct cga tcg cat ggg      378
Leu Pro Lys Val Glu Thr Glu Ala Leu Gly Leu Ala Arg Ser His Gly
             45                  50                  55 gaa cag ggc cag atg ccg gaa aac atg caa gtg tct caa ttt aaa atg      426
Glu Gln Gly Gln Met Pro Glu Asn Met Gln Val Ser Gln Phe Lys Met
             60                  65                  70 gtg aat tac tcc tat gat gaa gat ctg gaa gaa ctt tgt ccc gtg tgt      474
Val Asn Tyr Ser Tyr Asp Glu Asp Leu Glu Glu Leu Cys Pro Val Cys
 75                  80                  85 gga gat aaa gtg tct ggg tac cat tat ggg ctc ctc acc tgt gaa agc      522
Gly Asp Lys Val Ser Gly Tyr His Tyr Gly Leu Leu Thr Cys Glu Ser
 90                  95                 100                 105 tgc aag gga ttt ttt aag cga aca gtc caa aat aat aaa agg tac aca      570
Cys Lys Gly Phe Phe Lys Arg Thr Val Gln Asn Asn Lys Arg Tyr Thr
                110                 115                 120 tgt ata gaa aac cag aac tgc caa att gac aaa aca cag aga aag cgt      618
Cys Ile Glu Asn Gln Asn Cys Gln Ile Asp Lys Thr Gln Arg Lys Arg
             125                 130                 135 tgt cct tac tgt cgt ttt caa aaa tgt cta agt gtt gga atg aag cta      666
Cys Pro Tyr Cys Arg Phe Gln Lys Cys Leu Ser Val Gly Met Lys Leu
            140                 145                 150 gaa gct gta agg gcc gac cga atg cgt gga gga agg aat aag ttt ggg      714
Glu Ala Val Arg Ala Asp Arg Met Arg Gly Gly Arg Asn Lys Phe Gly
            155                 160                 165 cca atg tac aag aga gac agg gcc ctg aag caa cag aaa aaa gcc ctc      762
Pro Met Tyr Lys Arg Asp Arg Ala Leu Lys Gln Gln Lys Lys Ala Leu
170                 175                 180                 185 atc cga gcc aat gga ctt aag cta gaa gcc atg tct cag gtg atc caa      810
Ile Arg Ala Asn Gly Leu Lys Leu Glu Ala Met Ser Gln Val Ile Gln
                190                 195                 200 gct atg ccc tct gac ctg acc att tcc tct gca att caa aac atc cac      858
Ala Met Pro Ser Asp Leu Thr Ile Ser Ser Ala Ile Gln Asn Ile His
            205                 210                 215 tct gcc tcc aaa ggc cta cct ctg aac cat gct gcc ttg cct cct aca      906
Ser Ala Ser Lys Gly Leu Pro Leu Asn His Ala Ala Leu Pro Pro Thr
            220                 225                 230 gac tat gac aga agt ccc ttt gta aca tcc ccc att agc atg aca atg      954
Asp Tyr Asp Arg Ser Pro Phe Val Thr Ser Pro Ile Ser Met Thr Met
            235                 240                 245 ccc cct cac ggc agc ctg caa ggt tac caa aca tat ggc cac ttt cct     1002
Pro Pro His Gly Ser Leu Gln Gly Tyr Gln Thr Tyr Gly His Phe Pro
250                 255                 260                 265 agc cgg gcc atc aag tct gag tac cca gac ccc tat acc agc tca ccc     1050
Ser Arg Ala Ile Lys Ser Glu Tyr Pro Asp Pro Tyr Thr Ser Ser Pro
                270                 275                 280 gag tcc ata atg ggc tat tca tat atg gat agt tac cag acg agc tct     1098
Glu Ser Ile Met Gly Tyr Ser Tyr Met Asp Ser Tyr Gln Thr Ser Ser
            285                 290                 295 cca gca agc atc cca cat ctg ata ctg gaa ctt ttg aag tgt gag cca     1146
Pro Ala Ser Ile Pro His Leu Ile Leu Glu Leu Leu Lys Cys Glu Pro
            300                 305                 310 gat gag cct caa gtc cag gct aaa atc atg gcc tat ttg cag caa gag     1194
Asp Glu Pro Gln Val Gln Ala Lys Ile Met Ala Tyr Leu Gln Gln Glu
            315                 320                 325 cag gct aac cga agc aag cac gaa aag ctg agc acc ttt ggg ctt atg     1242
Gln Ala Asn Arg Ser Lys His Glu Lys Leu Ser Thr Phe Gly Leu Met
330                 335                 340                 345
```

```
tgc aaa atg gca gat caa act ctc ttc tcc att gtc gag tgg gcc agg          1290
Cys Lys Met Ala Asp Gln Thr Leu Phe Ser Ile Val Glu Trp Ala Arg
            350                 355                 360 agt agt atc ttc ttc aga gaa ctt aag gtt gat gac caa atg aag ctg          1338
Ser Ser Ile Phe Phe Arg Glu Leu Lys Val Asp Asp Gln Met Lys Leu
            365                 370                 375 ctt cag aac tgc tgg agt gag ctc tta atc ctc gac cac att tac cga          1386
Leu Gln Asn Cys Trp Ser Glu Leu Leu Ile Leu Asp His Ile Tyr Arg
            380                 385                 390 caa gtg gta cat gga aag gaa gga tcc atc ttc ctg gtt act ggg caa          1434
Gln Val Val His Gly Lys Glu Gly Ser Ile Phe Leu Val Thr Gly Gln
    395                 400                 405 caa gtg gac tat tcc ata ata gca tca caa gcc gga gcc acc ctc aac          1482
Gln Val Asp Tyr Ser Ile Ile Ala Ser Gln Ala Gly Ala Thr Leu Asn
410                 415                 420                 425 aac ctc atg agt cat gca cag gag tta gtg gca aaa ctt cgt tct ctc          1530
Asn Leu Met Ser His Ala Gln Glu Leu Val Ala Lys Leu Arg Ser Leu
            430                 435                 440 cag ttt gat caa cga gag ttc gta tgt ctg aaa ttc ttg gtg ctc ttt          1578
Gln Phe Asp Gln Arg Glu Phe Val Cys Leu Lys Phe Leu Val Leu Phe
            445                 450                 455 agt tta gat gtc aaa aac ctt gaa aac ttc cag ctg gta gaa ggt gtc          1626
Ser Leu Asp Val Lys Asn Leu Glu Asn Phe Gln Leu Val Glu Gly Val
            460                 465                 470 cag gaa caa gtc aat gcc gcc ctg ctg gac tac aca atg tgt aac tac          1674
Gln Glu Gln Val Asn Ala Ala Leu Leu Asp Tyr Thr Met Cys Asn Tyr
    475                 480                 485 ccg cag cag aca gag aaa ttt gga cag cta ctt ctt cga cta ccc gaa          1722
Pro Gln Gln Thr Glu Lys Phe Gly Gln Leu Leu Leu Arg Leu Pro Glu
490                 495                 500                 505 atc cgg gcc atc agt atg cag gct gaa gaa tac ctc tac tac aag cac          1770
Ile Arg Ala Ile Ser Met Gln Ala Glu Glu Tyr Leu Tyr Tyr Lys His
            510                 515                 520 ctg aac ggg gat gtg ccc tat aat aac ctt ctc att gaa atg ttg cat          1818
Leu Asn Gly Asp Val Pro Tyr Asn Asn Leu Leu Ile Glu Met Leu His
            525                 530                 535 gcc aaa aga gca taagttacaa ccccctaggag ctctgctttc aaaacaaaaa            1870
Ala Lys Arg Ala
            540 gagattgggg gagtgggag ggggaagaag aacaggaaga aaaaaagtac tctgaactgc         1930 tccaagcaac gctaattaaa aacttgcttt aaagatattg aatttaaaaa ggcataataa        1990 tcaaatactt aatagcaaat aaatgatgta tcagggtatt tgtattgcaa actgtgaatc       2050 aaaggcttca cagccccaga ggattccata taaaagacat tgtaatggag tggattgaac      2110 tcacagatgg ataccaacac ggtcagaaga aaaacggaca gaacggttct tgtatattta      2170 aactgatctc cactatgaag aaatttagga actaatctta ttaattaggc ttatacagcg      2230 ggggatttga gcttacagga ttcctccatg gtaaagctga actgaaacaa ttctcaagaa      2290 tgcatcagct gtacctacaa tagcccctcc ctcttccttt gaaggcccga gcacctctgc      2350 cctgtggtca ccgaatctgt actaaggacc tgtgttcagc cacacccagt ggtagctcca      2410 ccaaatcatg aacagcctaa ttttgagtgt ctgtgtctta gacctgcaaa cagctaatag      2470 gaaattctat taatatgtta gcttgccatt ttaaatatgt tctgagggtt gttttgtctc      2530 gtgttcatga tgttaagaaa atgcaggcag tatccctcat cttatgtaag tgtgaattaa      2590 tattaaggga aatgactaca aactttcaaa gcaaatgctc catagctaaa gcaacttaga      2650 ccttatttct gctactgttg ctgaaatgtg gctttggcat tgttggattt cataaaaaat       2710
```

```
ttctggcagg aagtcttgtt agtatacatc agtcttttt c atcatccaag tttgtagttc    2770
atttaaaaat acaacattaa acacattttg ctaggatgtc aaatagtcac agttctaagt    2830
agttggaaac aaaattgacg catgttaatc tatgcaaaga gaaggaaag gatgaggtga    2890 tgtattgact caaggttcat tcttgctgca attgaacatc ctcaagagtt gggatggaaa    2950
tggtgatttt tacatgtgtc ctggaaagat attaaagtaa ttcaaatctt ccccaaaggg    3010
gaaaggaaga gagtgatact gaccttttta agtcatagac caaagtctgc tgtagaacaa    3070
atatgggagg acaaagaatc gcaaattctt caaatgacta ttatcagtat tattaacatg    3130
cgatgccaca ggtatgaaag tcttgcctta tttcacaatt ttaaaaggta gctgtgcaga    3190
tgtggatcaa catttgttta aaataaagta ttaatacttt aaagtcaaaa aaaaaaaaa    3250 a                                                                    3251
```

<210> SEQ ID NO 6
<211> LENGTH: 541
<212> TYPE: PRT
<213> ORGANISM: human

<400> SEQUENCE: 6

```
Met Ser Ser Asn Ser Asp Thr Gly Asp Leu Gln Glu Ser Leu Lys His
  1               5                  10                  15

Gly Leu Thr Pro Ile Gly Ala Gly Leu Pro Asp Arg His Gly Ser Pro
                 20                  25                  30

Ile Pro Ala Arg Gly Arg Leu Val Met Leu Pro Lys Val Glu Thr Glu
             35                  40                  45

Ala Leu Gly Leu Ala Arg Ser His Gly Glu Gln Gly Gln Met Pro Glu
         50                  55                  60

Asn Met Gln Val Ser Gln Phe Lys Met Val Asn Tyr Ser Tyr Asp Glu
 65                  70                  75                  80

Asp Leu Glu Glu Leu Cys Pro Val Cys Gly Asp Lys Val Ser Gly Tyr
                 85                  90                  95

His Tyr Gly Leu Leu Thr Cys Glu Ser Cys Lys Gly Phe Phe Lys Arg
                100                 105                 110

Thr Val Gln Asn Asn Lys Arg Tyr Thr Cys Ile Glu Asn Gln Asn Cys
            115                 120                 125

Gln Ile Asp Lys Thr Gln Arg Lys Arg Cys Pro Tyr Cys Arg Phe Gln
        130                 135                 140

Lys Cys Leu Ser Val Gly Met Lys Leu Glu Ala Val Arg Ala Asp Arg
145                 150                 155                 160

Met Arg Gly Gly Arg Asn Lys Phe Gly Pro Met Tyr Lys Arg Asp Arg
                165                 170                 175

Ala Leu Lys Gln Gln Lys Lys Ala Leu Ile Arg Ala Asn Gly Leu Lys
            180                 185                 190

Leu Glu Ala Met Ser Gln Val Ile Gln Ala Met Pro Ser Asp Leu Thr
        195                 200                 205

Ile Ser Ser Ala Ile Gln Asn Ile His Ser Ala Ser Lys Gly Leu Pro
    210                 215                 220

Leu Asn His Ala Ala Leu Pro Pro Thr Asp Tyr Asp Arg Ser Pro Phe
225                 230                 235                 240

Val Thr Ser Pro Ile Ser Met Thr Met Pro Pro His Gly Ser Leu Gln
                245                 250                 255

Gly Tyr Gln Thr Tyr Gly His Phe Pro Ser Arg Ala Ile Lys Ser Glu
            260                 265                 270
```

```
Tyr Pro Asp Pro Tyr Thr Ser Ser Pro Glu Ser Ile Met Gly Tyr Ser
            275                 280                 285

Tyr Met Asp Ser Tyr Gln Thr Ser Ser Pro Ala Ser Ile Pro His Leu
        290                 295                 300

Ile Leu Glu Leu Leu Lys Cys Glu Pro Asp Glu Pro Gln Val Gln Ala
305                 310                 315                 320

Lys Ile Met Ala Tyr Leu Gln Gln Glu Gln Ala Asn Arg Ser Lys His
                325                 330                 335

Glu Lys Leu Ser Thr Phe Gly Leu Met Cys Lys Met Ala Asp Gln Thr
            340                 345                 350

Leu Phe Ser Ile Val Glu Trp Ala Arg Ser Ser Ile Phe Phe Arg Glu
        355                 360                 365

Leu Lys Val Asp Asp Gln Met Lys Leu Leu Gln Asn Cys Trp Ser Glu
370                 375                 380

Leu Leu Ile Leu Asp His Ile Tyr Arg Gln Val Val His Gly Lys Glu
385                 390                 395                 400

Gly Ser Ile Phe Leu Val Thr Gly Gln Gln Val Asp Tyr Ser Ile Ile
                405                 410                 415

Ala Ser Gln Ala Gly Ala Thr Leu Asn Asn Leu Met Ser His Ala Gln
            420                 425                 430

Glu Leu Val Ala Lys Leu Arg Ser Leu Gln Phe Asp Gln Arg Glu Phe
        435                 440                 445

Val Cys Leu Lys Phe Leu Val Leu Phe Ser Leu Asp Val Lys Asn Leu
450                 455                 460

Glu Asn Phe Gln Leu Val Glu Gly Val Gln Glu Gln Val Asn Ala Ala
465                 470                 475                 480

Leu Leu Asp Tyr Thr Met Cys Asn Tyr Pro Gln Gln Thr Glu Lys Phe
                485                 490                 495

Gly Gln Leu Leu Leu Arg Leu Pro Glu Ile Arg Ala Ile Ser Met Gln
            500                 505                 510

Ala Glu Glu Tyr Leu Tyr Tyr Lys His Leu Asn Gly Asp Val Pro Tyr
        515                 520                 525

Asn Asn Leu Leu Ile Glu Met Leu His Ala Lys Arg Ala
            530                 535                 540

<210> SEQ ID NO 7
<211> LENGTH: 2330
<212> TYPE: DNA
<213> ORGANISM: human
<220> FEATURE:
<221> NAME/KEY: CDS
<222> LOCATION: (363)..(1862)

<400> SEQUENCE: 7
gaaactggat acatggttta cagcaggtca ctaatgttgg aaaaagtaca gagtccaggg      60
aaagacttgc ttgtaacttt atgaattctg gattttttt cctttgcttt ttcttaactt     120
tcactaaggg ttactgtagt ctgatgtgtc cttcccaagg ccacgaaatt tgacaagctg     180
cactttcctt ttgctcaatg atttctgctt taagccaaag aactgcctat aatttcacta     240
agaatgtctt ctaattcaga tactggggat ttacaagagt ctttaaagca cggacttaca     300
cctattggtg ctgggcttcc ggaccgacac ggatccccca tcccgcccgc ggtcgccttg     360 tc atg ctg ccc aaa gtg gag acg gaa gcc ctg gga ctg gct cga tcg        407
   Met Leu Pro Lys Val Glu Thr Glu Ala Leu Gly Leu Ala Arg Ser
    1               5                   10                  15 cat ggg gaa cag ggc cag atg ccg gaa aac atg caa gtg tct caa ttt       455
His Gly Glu Gln Gly Gln Met Pro Glu Asn Met Gln Val Ser Gln Phe
```

-continued

|  | 20 | 25 | 30 |  |
|---|---|---|---|---|
| aaa atg gtg aat tac tcc tat gat gaa gat ctg gaa gag ctt tgt ccc | | | | 503 |
| Lys Met Val Asn Tyr Ser Tyr Asp Glu Asp Leu Glu Glu Leu Cys Pro | | | | |
|  | 35 | 40 | 45 |  |

| gtg tgt gga gat aaa gtg tct ggg tac cat tat ggg ctc ctc acc tgt | 551 |
| Val Cys Gly Asp Lys Val Ser Gly Tyr His Tyr Gly Leu Leu Thr Cys | |
| 50 55 60 | |

| gaa agc tgc aag gga ttt ttt aag cga aca gtc caa aat aat aaa agg | 599 |
| Glu Ser Cys Lys Gly Phe Phe Lys Arg Thr Val Gln Asn Asn Lys Arg | |
| 65 70 75 | |

| tac aca tgt ata gaa aac cag aac tgc caa att gac aaa aca cag aga | 647 |
| Tyr Thr Cys Ile Glu Asn Gln Asn Cys Gln Ile Asp Lys Thr Gln Arg | |
| 80 85 90 95 | |

| aag cgt tgt cct tac tgt cgt ttt caa aaa tgt cta agt gtt gga atg | 695 |
| Lys Arg Cys Pro Tyr Cys Arg Phe Gln Lys Cys Leu Ser Val Gly Met | |
| 100 105 110 | |

| aag cta gaa gct gta agg gcc gac cga atg cgt gga gga agg aat aag | 743 |
| Lys Leu Glu Ala Val Arg Ala Asp Arg Met Arg Gly Gly Arg Asn Lys | |
| 115 120 125 | |

| ttt ggg cca atg tac aag aga gac agg gcc ctg aag caa cag aaa aaa | 791 |
| Phe Gly Pro Met Tyr Lys Arg Asp Arg Ala Leu Lys Gln Gln Lys Lys | |
| 130 135 140 | |

| gcc ctc atc cga gcc aat gga ctt aag cta gaa gcc atg tct cag gtg | 839 |
| Ala Leu Ile Arg Ala Asn Gly Leu Lys Leu Glu Ala Met Ser Gln Val | |
| 145 150 155 | |

| atc caa gct atg ccc tct gac ctg acc att tcc tct gca att caa aac | 887 |
| Ile Gln Ala Met Pro Ser Asp Leu Thr Ile Ser Ser Ala Ile Gln Asn | |
| 160 165 170 175 | |

| atc cac tct gcc tcc aaa ggc cta cct ctg aac cat gct gcc ttg cct | 935 |
| Ile His Ser Ala Ser Lys Gly Leu Pro Leu Asn His Ala Ala Leu Pro | |
| 180 185 190 | |

| cct aca gac tat gac aga agt ccc ttt gta aca tcc ccc att agc atg | 983 |
| Pro Thr Asp Tyr Asp Arg Ser Pro Phe Val Thr Ser Pro Ile Ser Met | |
| 195 200 205 | |

| aca atg ctg cac ggc agc ctg caa ggt tac caa aca tat ggc cac ttt | 1031 |
| Thr Met Leu His Gly Ser Leu Gln Gly Tyr Gln Thr Tyr Gly His Phe | |
| 210 215 220 | |

| cct agc cgg gcc atc aag tct gag tac cca gac ccc tat acc agc tca | 1079 |
| Pro Ser Arg Ala Ile Lys Ser Glu Tyr Pro Asp Pro Tyr Thr Ser Ser | |
| 225 230 235 | |

| ccc gag tcc ata atg ggc tat tca tat atg gat agt tac cag acg agc | 1127 |
| Pro Glu Ser Ile Met Gly Tyr Ser Tyr Met Asp Ser Tyr Gln Thr Ser | |
| 240 245 250 255 | |

| tct cca gca agc atc cca cat ctg ata ctg gaa ctt ttg aag tgt gag | 1175 |
| Ser Pro Ala Ser Ile Pro His Leu Ile Leu Glu Leu Leu Lys Cys Glu | |
| 260 265 270 | |

| cca gat gag cct caa gtc cag gct aaa atc atg gcc tat ttg cag caa | 1223 |
| Pro Asp Glu Pro Gln Val Gln Ala Lys Ile Met Ala Tyr Leu Gln Gln | |
| 275 280 285 | |

| gag cag gct aac cga agc aag cac gaa aag ctg agc acc ttt ggg ctt | 1271 |
| Glu Gln Ala Asn Arg Ser Lys His Glu Lys Leu Ser Thr Phe Gly Leu | |
| 290 295 300 | |

| atg tgc aaa atg gca gat caa act gtc ttc tcc att gtc gag tgg gcc | 1319 |
| Met Cys Lys Met Ala Asp Gln Thr Val Phe Ser Ile Val Glu Trp Ala | |
| 305 310 315 | |

| agg agt agt atc ttc ttc aga gaa ctt aag gtt gat gac caa atg aag | 1367 |
| Arg Ser Ser Ile Phe Phe Arg Glu Leu Lys Val Asp Asp Gln Met Lys | |
| 320 325 330 335 | |

| ctg ctt cag aac tgc tgg agt gag ctc tta atc ctc gac cac att tac | 1415 |
| Leu Leu Gln Asn Cys Trp Ser Glu Leu Leu Ile Leu Asp His Ile Tyr | |

-continued

```
          340                 345                 350
cga caa gtg gta cat gga aag gaa gga tcc atc ttc ctg gtt act ggg    1463
Arg Gln Val Val His Gly Lys Glu Gly Ser Ile Phe Leu Val Thr Gly
            355                 360                 365 caa caa gtg gac tat tcc ata ata gca tca caa gcc gga gcc acc ctc    1511
Gln Gln Val Asp Tyr Ser Ile Ile Ala Ser Gln Ala Gly Ala Thr Leu
        370                 375                 380 aac aac ctc atg agt cat gca cag gag tta gtg gca aaa ctt cgt tct    1559
Asn Asn Leu Met Ser His Ala Gln Glu Leu Val Ala Lys Leu Arg Ser
    385                 390                 395 ctc cag ttt gat caa cga gag ttc gta tgt ctg aaa ttc ttg gtg ctc    1607
Leu Gln Phe Asp Gln Arg Glu Phe Val Cys Leu Lys Phe Leu Val Leu
400                 405                 410                 415 ttt agt tta gat gtc aaa aac ctt gaa aac ttc cag ctg gta gaa ggt    1655
Phe Ser Leu Asp Val Lys Asn Leu Glu Asn Phe Gln Leu Val Glu Gly
                420                 425                 430 gtc cag gaa caa gtc aat gcc gcc ctg ctg gac tac aca atg tgt aac    1703
Val Gln Glu Gln Val Asn Ala Ala Leu Leu Asp Tyr Thr Met Cys Asn
            435                 440                 445 tac ccg cag cag aca gag aaa ttt gga cag cta ctt ctt cga cta ccc    1751
Tyr Pro Gln Gln Thr Glu Lys Phe Gly Gln Leu Leu Leu Arg Leu Pro
        450                 455                 460 gaa atc cgg gcc atc agt atg cag gct gaa gaa tac ctc tac tac aag    1799
Glu Ile Arg Ala Ile Ser Met Gln Ala Glu Glu Tyr Leu Tyr Tyr Lys
    465                 470                 475 cac ctg aat ggg gat gtg ccc tat aat aac ctt ctc att gaa atg ttg    1847
His Leu Asn Gly Asp Val Pro Tyr Asn Asn Leu Leu Ile Glu Met Leu
480                 485                 490                 495 cat gcc aaa aga gca taagttacaa cccctaggag ctctgctttc aaaacaaaaa    1902
His Ala Lys Arg Ala
                500 gagattgggg gagtggggag ggggaagaag aacaggaaga aaaaaagtac tctgaactgc    1962 tccaagtaac gctaattaaa aacttgcttt aaagatattg aatttaaaaa ggcataataa    2022 tcaaatacta atagcaaata aatgatgtat cagggtattt gtattgcaaa ctgtgaatca    2082 aagcttcaca gccccagagg attccatata aaagacattg taatggagtg gattgaactc    2142 acagatggat accaacacgg tcagaagaaa acggacaga acggttcttg tatatttaaa    2202 ctgatctcca ctatgaagaa atttaggaac taatcttatt aattaggctt atacagcggg    2262 gatttgagct tacaggattc ctccatggta aagctgaact gaaacaattc tcaagaatgc    2322 atcagctg                                                            2330

<210> SEQ ID NO 8
<211> LENGTH: 500
<212> TYPE: PRT
<213> ORGANISM: human

<400> SEQUENCE: 8

Met Leu Pro Lys Val Glu Thr Glu Ala Leu Gly Leu Ala Arg Ser His
  1               5                  10                  15

Gly Glu Gln Gly Gln Met Pro Glu Asn Met Gln Val Ser Gln Phe Lys
             20                  25                  30

Met Val Asn Tyr Ser Tyr Asp Glu Asp Leu Glu Glu Leu Cys Pro Val
         35                  40                  45

Cys Gly Asp Lys Val Ser Gly Tyr His Tyr Gly Leu Leu Thr Cys Glu
     50                  55                  60

Ser Cys Lys Gly Phe Phe Lys Arg Thr Val Gln Asn Asn Lys Arg Tyr
 65                  70                  75                  80
```

```
Thr Cys Ile Glu Asn Gln Asn Cys Gln Ile Asp Lys Thr Gln Arg Lys
                85                  90                  95

Arg Cys Pro Tyr Cys Arg Phe Gln Lys Cys Leu Ser Val Gly Met Lys
            100                 105                 110

Leu Glu Ala Val Arg Ala Asp Arg Met Arg Gly Gly Arg Asn Lys Phe
        115                 120                 125

Gly Pro Met Tyr Lys Arg Asp Arg Ala Leu Lys Gln Gln Lys Lys Ala
    130                 135                 140

Leu Ile Arg Ala Asn Gly Leu Lys Leu Glu Ala Met Ser Gln Val Ile
145                 150                 155                 160

Gln Ala Met Pro Ser Asp Leu Thr Ile Ser Ser Ala Ile Gln Asn Ile
                165                 170                 175

His Ser Ala Ser Lys Gly Leu Pro Leu Asn His Ala Ala Leu Pro Pro
            180                 185                 190

Thr Asp Tyr Asp Arg Ser Pro Phe Val Thr Ser Pro Ile Ser Met Thr
        195                 200                 205

Met Leu His Gly Ser Leu Gln Gly Tyr Gln Thr Tyr Gly His Phe Pro
    210                 215                 220

Ser Arg Ala Ile Lys Ser Glu Tyr Pro Asp Pro Tyr Thr Ser Ser Pro
225                 230                 235                 240

Glu Ser Ile Met Gly Tyr Ser Tyr Met Asp Ser Tyr Gln Thr Ser Ser
                245                 250                 255

Pro Ala Ser Ile Pro His Leu Ile Leu Glu Leu Leu Lys Cys Glu Pro
            260                 265                 270

Asp Glu Pro Gln Val Gln Ala Lys Ile Met Ala Tyr Leu Gln Gln Glu
        275                 280                 285

Gln Ala Asn Arg Ser Lys His Glu Lys Leu Ser Thr Phe Gly Leu Met
    290                 295                 300

Cys Lys Met Ala Asp Gln Thr Val Phe Ser Ile Val Glu Trp Ala Arg
305                 310                 315                 320

Ser Ser Ile Phe Phe Arg Glu Leu Lys Val Asp Asp Gln Met Lys Leu
                325                 330                 335

Leu Gln Asn Cys Trp Ser Glu Leu Leu Ile Leu Asp His Ile Tyr Arg
            340                 345                 350

Gln Val Val His Gly Lys Glu Gly Ser Ile Phe Leu Val Thr Gly Gln
        355                 360                 365

Gln Val Asp Tyr Ser Ile Ile Ala Ser Gln Ala Gly Ala Thr Leu Asn
    370                 375                 380

Asn Leu Met Ser His Ala Gln Glu Leu Val Ala Lys Leu Arg Ser Leu
385                 390                 395                 400

Gln Phe Asp Gln Arg Glu Phe Val Cys Leu Lys Phe Leu Val Leu Phe
                405                 410                 415

Ser Leu Asp Val Lys Asn Leu Glu Asn Phe Gln Leu Val Glu Gly Val
            420                 425                 430

Gln Glu Gln Val Asn Ala Ala Leu Leu Asp Tyr Thr Met Cys Asn Tyr
        435                 440                 445

Pro Gln Gln Thr Glu Lys Phe Gly Gln Leu Leu Leu Arg Leu Pro Glu
    450                 455                 460

Ile Arg Ala Ile Ser Met Gln Ala Glu Glu Tyr Leu Tyr Tyr Lys His
465                 470                 475                 480

Leu Asn Gly Asp Val Pro Tyr Asn Asn Leu Leu Ile Glu Met Leu His
                485                 490                 495

Ala Lys Arg Ala
```

-continued

```
                            500

<210> SEQ ID NO 9
<211> LENGTH: 3027
<212> TYPE: DNA
<213> ORGANISM: human
<220> FEATURE:
<221> NAME/KEY: CDS
<222> LOCATION: (159)..(1838)

<400> SEQUENCE: 9
tgttttttcc ccctttttct taactttcac taaggaaatg agggttactg tagtctgagg       60
tttccttccc aaagtcacaa aatatgacaa gctgcaatct ttctcacatt caatgatttc      120
tgctgtaagc caaaggactg ccaataattt cgctaaga atg tct gct agt ttg gat      176
                                           Met Ser Ala Ser Leu Asp
                                             1               5 act gga gat ttt caa gaa ttt ctt aag cat gga ctt aca gct att gcg        224
Thr Gly Asp Phe Gln Glu Phe Leu Lys His Gly Leu Thr Ala Ile Ala
                10                  15                  20 tct gca cca ggg tca gag act cgc cac tcc ccc aaa cgt gag gaa caa        272
Ser Ala Pro Gly Ser Glu Thr Arg His Ser Pro Lys Arg Glu Glu Gln
         25                  30                  35 ctc cgg gaa aaa cgt gct ggg ctt ccg gac cga cac cga cgc ccc att        320
Leu Arg Glu Lys Arg Ala Gly Leu Pro Asp Arg His Arg Arg Pro Ile
 40                  45                  50 ccc gcc cgc agc cgc ctt gtc atg ctg ccc aaa gtg gag acg gaa gcc        368
Pro Ala Arg Ser Arg Leu Val Met Leu Pro Lys Val Glu Thr Glu Ala
 55                  60                  65                  70 cca gga ctg gtc cga tcg cat ggg gaa cag ggg cag atg cca gaa aac        416
Pro Gly Leu Val Arg Ser His Gly Glu Gln Gly Gln Met Pro Glu Asn
                 75                  80                  85 atg caa gtg tct caa ttt aaa atg gtg aat tac tcc tat gat gaa gat        464
Met Gln Val Ser Gln Phe Lys Met Val Asn Tyr Ser Tyr Asp Glu Asp
         90                  95                 100 ctg gaa gag cta tgt cct gtg tgt ggc gat aaa gtg tct ggg tac cat        512
Leu Glu Glu Leu Cys Pro Val Cys Gly Asp Lys Val Ser Gly Tyr His
    105                 110                 115 tac ggt ctc ctc acg tgc gaa agc tgc aag ggt ttt ttt aag cga act        560
Tyr Gly Leu Leu Thr Cys Glu Ser Cys Lys Gly Phe Phe Lys Arg Thr
120                 125                 130 gtc caa aac caa aaa agg tac acg tgc ata gag aac cag aat tgc caa        608
Val Gln Asn Gln Lys Arg Tyr Thr Cys Ile Glu Asn Gln Asn Cys Gln
135                 140                 145                 150 att gac aaa acg cag aga aaa cga tgt ccc tac tgt cga ttc aaa aaa        656
Ile Asp Lys Thr Gln Arg Lys Arg Cys Pro Tyr Cys Arg Phe Lys Lys
                155                 160                 165 tgt atc gat gtt ggg atg aag ctg gaa gcc gta aga gcc gac cgc atg        704
Cys Ile Asp Val Gly Met Lys Leu Glu Ala Val Arg Ala Asp Arg Met
        170                 175                 180 cga ggg ggc aga aat aag ttt ggg cca atg tac aag aga gac agg gct        752
Arg Gly Gly Arg Asn Lys Phe Gly Pro Met Tyr Lys Arg Asp Arg Ala
    185                 190                 195 ttg aag cag cag aag aaa gcc ctc att cga gcc aat gga ctt aag ctg        800
Leu Lys Gln Gln Lys Lys Ala Leu Ile Arg Ala Asn Gly Leu Lys Leu
200                 205                 210 gaa gcc atg tct cag gtg atc caa gca atg ccc tca gac ctg acc tct        848
Glu Ala Met Ser Gln Val Ile Gln Ala Met Pro Ser Asp Leu Thr Ser
215                 220                 225                 230 gca att cag aac att cat tcc gcc tcc aaa ggc cta cct ctg agc cat        896
Ala Ile Gln Asn Ile His Ser Ala Ser Lys Gly Leu Pro Leu Ser His
                235                 240                 245
```

```
gta gcc ttg cct ccg aca gac tat gac aga agt ccc ttt gtc aca tct      944
Val Ala Leu Pro Pro Thr Asp Tyr Asp Arg Ser Pro Phe Val Thr Ser
            250                 255                 260 ccc att agc atg aca atg cca cct cac agc agc ctg cat ggt tac caa      992
Pro Ile Ser Met Thr Met Pro Pro His Ser Ser Leu His Gly Tyr Gln
            265                 270                 275 ccc tat ggt cac ttt cct agt cgg gcc atc aag tct gag tac cca gac     1040
Pro Tyr Gly His Phe Pro Ser Arg Ala Ile Lys Ser Glu Tyr Pro Asp
            280                 285                 290 ccc tac tcc agc tca cct gag tca atg atg ggt tac tcc tac atg gat     1088
Pro Tyr Ser Ser Ser Pro Glu Ser Met Met Gly Tyr Ser Tyr Met Asp
295                 300                 305                 310 ggt tac cag aca aac tcc ccg gcc agc atc cca cac ctg ata ctg gaa     1136
Gly Tyr Gln Thr Asn Ser Pro Ala Ser Ile Pro His Leu Ile Leu Glu
                315                 320                 325 ctt ttg aag tgt gaa cca gat gag cct caa gtt caa gcg aag atc atg     1184
Leu Leu Lys Cys Glu Pro Asp Glu Pro Gln Val Gln Ala Lys Ile Met
                330                 335                 340 gct tac ctc cag caa gag cag agt aac cga aac agg caa gaa aag ctg     1232
Ala Tyr Leu Gln Gln Glu Gln Ser Asn Arg Asn Arg Gln Glu Lys Leu
                345                 350                 355 agc gca ttt ggg ctt tta tgc aaa atg gcg gac cag acc ctg ttc tcc     1280
Ser Ala Phe Gly Leu Leu Cys Lys Met Ala Asp Gln Thr Leu Phe Ser
            360                 365                 370 att gtt gag tgg gcc agg agt agt atc ttc ttc agg gaa ctg aag gtt     1328
Ile Val Glu Trp Ala Arg Ser Ser Ile Phe Phe Arg Glu Leu Lys Val
375                 380                 385                 390 gat gac caa atg aag ctg ctt caa aac tgc tgg agt gag ctc ttg att     1376
Asp Asp Gln Met Lys Leu Leu Gln Asn Cys Trp Ser Glu Leu Leu Ile
                395                 400                 405 ctc gat cac att tac cga caa gtg gcg cat ggg aag gaa ggg aca atc     1424
Leu Asp His Ile Tyr Arg Gln Val Ala His Gly Lys Glu Gly Thr Ile
                410                 415                 420 ttc ctg gtt act gga gaa cac gtg gac tac tcc acc atc atc tca cac     1472
Phe Leu Val Thr Gly Glu His Val Asp Tyr Ser Thr Ile Ile Ser His
            425                 430                 435 aca gaa gtc gcg ttc aac aac ctc ctg agt ctc gca cag gag ctg gtg     1520
Thr Glu Val Ala Phe Asn Asn Leu Leu Ser Leu Ala Gln Glu Leu Val
            440                 445                 450 gtg agg ctc cgt tcc ctt cag ttc gat cag cgg gag ttt gta tgt ctc     1568
Val Arg Leu Arg Ser Leu Gln Phe Asp Gln Arg Glu Phe Val Cys Leu
455                 460                 465                 470 aag ttc ctg gtg ctg ttc agc tca gat gtg aag aac ctg gag aac ctg     1616
Lys Phe Leu Val Leu Phe Ser Ser Asp Val Lys Asn Leu Glu Asn Leu
                475                 480                 485 cag ctg gtg gaa ggt gtc caa gag cag gtg aat gcc gcc ctg ctg gac     1664
Gln Leu Val Glu Gly Val Gln Glu Gln Val Asn Ala Ala Leu Leu Asp
            490                 495                 500 tac acg gtt tgc aac tac cca caa cag act gag aaa ttc gga cag cta     1712
Tyr Thr Val Cys Asn Tyr Pro Gln Gln Thr Glu Lys Phe Gly Gln Leu
            505                 510                 515 ctt ctt cgg cta ccc gag atc cgg gca atc agc aag cag gca gaa gac     1760
Leu Leu Arg Leu Pro Glu Ile Arg Ala Ile Ser Lys Gln Ala Glu Asp
            520                 525                 530 tac ctg tac tat aag cac gtg aac ggg gat gtg ccc tat aat aac ctc     1808
Tyr Leu Tyr Tyr Lys His Val Asn Gly Asp Val Pro Tyr Asn Asn Leu
535                 540                 545                 550 ctc att gag atg ctg cat gcc aaa aga gcc taagtcccca cccctggaag       1858
Leu Ile Glu Met Leu His Ala Lys Arg Ala
                555                 560
```

-continued

```
cttgctctag gaacacagac tggaaggaga agaggaggac gatgacagaa acacaatact   1918
ctgaactgct ccaagcaatg ctaattataa acttggttta aagacactga attttaaaag   1978
cataataatt aaatacctaa tagcaaataa atgatatatc agggtatttg tactgcaaac   2038
tgtgaatcaa aggctgtatg aatcaaagga ttcatatgaa agacattgta atgggtgga    2098 ttgaacttac agatggagac caataccaca gcagaataaa aatggacaga acaatccttg   2158
tatatttaaa ctaatctgct attaagaaat tcagaagttg atctctgtta ttaattggat   2218
ttgtcctgaa ttactccgtg gtgacgctga acaactcaag aatacatggg ctgtgcttgg   2278
cagcccctcc ccatccctcc caccaccacc accccaccc ccacaaggcc ctataccttc    2338
tgacctgtga gccctgaagc tattttaagg acttctgttc agccataccc agtagtagct   2398
ccactaaacc atgatttctg gatgtctgtg tcttagacct gccaacagct aataagaaca   2458
atgtataaat atgtcagctt gcattttaaa tatgtgctga agtttgtttt gtcgtgtgtt   2518
cgtaattaaa aagaaaacgg gcagtaaccc tcttctatat aagcattagt taatattaag   2578
ggaaatcaaa caaatctaag ccaatactcc caacaagcaa gttagatctt acttctgctg   2638
ctgttgctga aatgtggctt tggcatggtt gggtttcata aaacttttg gccaagaggc    2698 ttgttagtat acatccatct gtttagtcat caaggtttgt agttcactta aaaaaaaata   2758
aaccactaga catcttttgc tgaatgtcaa atagtcacag tctaagtagc caaaaagtca   2818
aagcgtgtta acattgcca aatgaaggaa agggtgagct gcaaagggga tggttcgagg    2878
ttcattccag ttgtgacccg agcgtcccca aaacctggga tgcaaagaca gtgattctgc   2938
atatggcctg gaaagacagg aaagccagtc tcctacaaag gggaatggaa gatcctggcc   2998
tctaagtcat agaccaaagt ctgctgtag                                     3027
```

<210> SEQ ID NO 10
<211> LENGTH: 560
<212> TYPE: PRT
<213> ORGANISM: human

<400> SEQUENCE: 10

```
Met Ser Ala Ser Leu Asp Thr Gly Asp Phe Gln Glu Phe Leu Lys His
 1               5                  10                  15

Gly Leu Thr Ala Ile Ala Ser Ala Pro Gly Ser Glu Thr Arg His Ser
            20                  25                  30

Pro Lys Arg Glu Glu Gln Leu Arg Glu Lys Arg Ala Gly Leu Pro Asp
        35                  40                  45

Arg His Arg Arg Pro Ile Pro Ala Arg Ser Arg Leu Val Met Leu Pro
    50                  55                  60

Lys Val Glu Thr Glu Ala Pro Gly Leu Val Arg Ser His Gly Glu Gln
65                  70                  75                  80

Gly Gln Met Pro Glu Asn Met Gln Val Ser Gln Phe Lys Met Val Asn
                85                  90                  95

Tyr Ser Tyr Asp Glu Asp Leu Glu Glu Leu Cys Pro Val Cys Gly Asp
            100                 105                 110

Lys Val Ser Gly Tyr His Tyr Gly Leu Leu Thr Cys Glu Ser Cys Lys
        115                 120                 125

Gly Phe Phe Lys Arg Thr Val Gln Asn Gln Lys Arg Tyr Thr Cys Ile
    130                 135                 140

Glu Asn Gln Asn Cys Gln Ile Asp Lys Thr Gln Arg Lys Arg Cys Pro
145                 150                 155                 160

Tyr Cys Arg Phe Lys Lys Cys Ile Asp Val Gly Met Lys Leu Glu Ala
```

165                 170                 175
Val Arg Ala Asp Arg Met Arg Gly Gly Arg Asn Lys Phe Gly Pro Met
                180                 185                 190

Tyr Lys Arg Asp Arg Ala Leu Lys Gln Gln Lys Lys Ala Leu Ile Arg
            195                 200                 205

Ala Asn Gly Leu Lys Leu Glu Ala Met Ser Gln Val Ile Gln Ala Met
        210                 215                 220

Pro Ser Asp Leu Thr Ser Ala Ile Gln Asn Ile His Ser Ala Ser Lys
225                 230                 235                 240

Gly Leu Pro Leu Ser His Val Ala Leu Pro Pro Thr Asp Tyr Asp Arg
                245                 250                 255

Ser Pro Phe Val Thr Ser Pro Ile Ser Met Thr Met Pro Pro His Ser
            260                 265                 270

Ser Leu His Gly Tyr Gln Pro Tyr Gly His Phe Pro Ser Arg Ala Ile
        275                 280                 285

Lys Ser Glu Tyr Pro Asp Pro Tyr Ser Ser Ser Pro Glu Ser Met Met
290                 295                 300

Gly Tyr Ser Tyr Met Asp Gly Tyr Gln Thr Asn Ser Pro Ala Ser Ile
305                 310                 315                 320

Pro His Leu Ile Leu Glu Leu Leu Lys Cys Glu Pro Asp Glu Pro Gln
                325                 330                 335

Val Gln Ala Lys Ile Met Ala Tyr Leu Gln Gln Glu Gln Ser Asn Arg
            340                 345                 350

Asn Arg Gln Glu Lys Leu Ser Ala Phe Gly Leu Leu Cys Lys Met Ala
        355                 360                 365

Asp Gln Thr Leu Phe Ser Ile Val Glu Trp Ala Arg Ser Ser Ile Phe
    370                 375                 380

Phe Arg Glu Leu Lys Val Asp Asp Gln Met Lys Leu Leu Gln Asn Cys
385                 390                 395                 400

Trp Ser Glu Leu Leu Ile Leu Asp His Ile Tyr Arg Gln Val Ala His
                405                 410                 415

Gly Lys Glu Gly Thr Ile Phe Leu Val Thr Gly Glu His Val Asp Tyr
            420                 425                 430

Ser Thr Ile Ile Ser His Thr Glu Val Ala Phe Asn Asn Leu Leu Ser
        435                 440                 445

Leu Ala Gln Glu Leu Val Val Arg Leu Arg Ser Leu Gln Phe Asp Gln
450                 455                 460

Arg Glu Phe Val Cys Leu Lys Phe Leu Val Leu Phe Ser Ser Asp Val
465                 470                 475                 480

Lys Asn Leu Glu Asn Leu Gln Leu Val Glu Gly Val Gln Glu Gln Val
                485                 490                 495

Asn Ala Ala Leu Leu Asp Tyr Thr Val Cys Asn Tyr Pro Gln Gln Thr
            500                 505                 510

Glu Lys Phe Gly Gln Leu Leu Leu Arg Leu Pro Glu Ile Arg Ala Ile
        515                 520                 525

Ser Lys Gln Ala Glu Asp Tyr Leu Tyr Tyr Lys His Val Asn Gly Asp
    530                 535                 540

Val Pro Tyr Asn Asn Leu Leu Ile Glu Met Leu His Ala Lys Arg Ala
545                 550                 555                 560

<210> SEQ ID NO 11
<211> LENGTH: 34
<212> TYPE: DNA
<213> ORGANISM: human

-continued

```
<400> SEQUENCE: 11 tctgataacct gtggacttag ttcaaggcca gtta                              34

<210> SEQ ID NO 12
<211> LENGTH: 34
<212> TYPE: DNA
<213> ORGANISM: human

<400> SEQUENCE: 12
tctggaggat gtggacttag ttcaaggcca gtta                              34

<210> SEQ ID NO 13
<211> LENGTH: 34
<212> TYPE: DNA
<213> ORGANISM: human

<400> SEQUENCE: 13 tctgataacct gttatattag ttcaaggcca gtta                             34

<210> SEQ ID NO 14
<211> LENGTH: 34
<212> TYPE: DNA
<213> ORGANISM: mouse

<400> SEQUENCE: 14
tctggaggat gtggacttct atcaaggcca gtta                              34

<210> SEQ ID NO 15
<211> LENGTH: 34
<212> TYPE: DNA
<213> ORGANISM: mouse

<400> SEQUENCE: 15 tctgataacct gttatattct atcaaggcca gtta                             34

<210> SEQ ID NO 16
<211> LENGTH: 34
<212> TYPE: DNA
<213> ORGANISM: human

<400> SEQUENCE: 16
tctggaggat gtggacttag ttcacacaga gtta                              34

<210> SEQ ID NO 17
<211> LENGTH: 34
<212> TYPE: DNA
<213> ORGANISM: human

<400> SEQUENCE: 17 tctgataacct gtggacttag tagaaggcca gtta                             34

<210> SEQ ID NO 18
<211> LENGTH: 34
<212> TYPE: DNA
<213> ORGANISM: human

<400> SEQUENCE: 18 tctgataacct gtggacttag ttcttggcca gtta                             34

<210> SEQ ID NO 19
<211> LENGTH: 34
<212> TYPE: DNA
<213> ORGANISM: human
```

-continued

```
<400> SEQUENCE: 19
tctgatacct gtggacttag ttcaatgcca gtta                              34

<210> SEQ ID NO 20
<211> LENGTH: 34
<212> TYPE: DNA
<213> ORGANISM: human

<400> SEQUENCE: 20
tctgatacct gtggacttag ttcaagtcca gtta                              34

<210> SEQ ID NO 21
<211> LENGTH: 34
<212> TYPE: DNA
<213> ORGANISM: human

<400> SEQUENCE: 21
tctgatacct gtggacttag ttcaaggaga gtta                              34

<210> SEQ ID NO 22
<211> LENGTH: 34
<212> TYPE: DNA
<213> ORGANISM: human

<400> SEQUENCE: 22
tctgatacct gtggacttag ttcaaggcct atta                              34

<210> SEQ ID NO 23
<211> LENGTH: 34
<212> TYPE: DNA
<213> ORGANISM: human

<400> SEQUENCE: 23
tctgatacct gtggacttag ttcaaggcca atta                              34

<210> SEQ ID NO 24
<211> LENGTH: 34
<212> TYPE: DNA
<213> ORGANISM: human

<400> SEQUENCE: 24
tctgatacct gtggacttag ttcaaggcca ggta                              34

<210> SEQ ID NO 25
<211> LENGTH: 34
<212> TYPE: DNA
<213> ORGANISM: human

<400> SEQUENCE: 25
tctgatacct gtggacttag tcaaggcca gtta                               34

<210> SEQ ID NO 26
<211> LENGTH: 34
<212> TYPE: DNA
<213> ORGANISM: human

<400> SEQUENCE: 26
tctgatacct gtggacttag taccaggcca gtta                              34

<210> SEQ ID NO 27
<211> LENGTH: 34
<212> TYPE: DNA
<213> ORGANISM: human
```

-continued

```
<400> SEQUENCE: 27
tctgatacct gtggacttag taggaggcca gtta                          34

<210> SEQ ID NO 28
<211> LENGTH: 34
<212> TYPE: DNA
<213> ORGANISM: human

<400> SEQUENCE: 28
tctgatacct gtggacttag taagaggcca gtta                          34

<210> SEQ ID NO 29
<211> LENGTH: 34
<212> TYPE: DNA
<213> ORGANISM: human

<400> SEQUENCE: 29
tctgatacct gtggacttag tttcaggcca gtta                          34

<210> SEQ ID NO 30
<211> LENGTH: 34
<212> TYPE: DNA
<213> ORGANISM: human

<400> SEQUENCE: 30
tctgatacct gtggacttag tctcaggcca gtta                          34
```